United States Patent
Ma et al.

(10) Patent No.: US 11,974,845 B2
(45) Date of Patent: *May 7, 2024

(54) SYSTEM AND METHOD FOR FACTORY CALIBRATION OR REDUCED CALIBRATION OF AN INDWELLING SENSOR BASED ON SENSITIVITY PROFILE AND BASELINE MODEL OF SENSORS

(71) Applicant: DexCom, Inc., San Diego, CA (US)

(72) Inventors: Rui Ma, San Diego, CA (US); Naresh C. Bhavaraju, San Diego, CA (US); Thomas Stuart Hamilton, Solana Beach, CA (US); Jonathan Hughes, Carlsbad, CA (US); Jeff Jackson, Poway, CA (US); David I-Chun Lee, San Diego, CA (US); Peter C. Simpson, Cardiff by the Sea, CA (US); Stephen J. Vanslyke, Carlsbad, CA (US)

(73) Assignee: Dexcom, Inc., San Diego, CA (US)

( * ) Notice: Subject to any disclaimer, the term of this patent is extended or adjusted under 35 U.S.C. 154(b) by 296 days.

This patent is subject to a terminal disclaimer.

(21) Appl. No.: 17/368,541

(22) Filed: Jul. 6, 2021

(65) Prior Publication Data

US 2021/0330219 A1    Oct. 28, 2021

Related U.S. Application Data

(63) Continuation of application No. 16/911,172, filed on Jun. 24, 2020, now Pat. No. 11,051,731, which is a
(Continued)

(51) Int. Cl.
*A61B 5/1495*    (2006.01)
*A61B 5/145*    (2006.01)
(Continued)

(52) U.S. Cl.
CPC ........ *A61B 5/1495* (2013.01); *A61B 5/14532* (2013.01); *G01N 33/66* (2013.01); *A61B 5/14865* (2013.01)

(58) Field of Classification Search
CPC .............. A61B 5/1495; A61B 5/14532; A61B 5/14865; G01N 33/66
See application file for complete search history.

(56) References Cited

U.S. PATENT DOCUMENTS 6,001,067 A    12/1999    Shults et al.
6,424,847 B1    7/2002    Mastrototaro et al.
(Continued)

FOREIGN PATENT DOCUMENTS

JP    2012519038 A    8/2012
JP    2012531948 A    12/2012
(Continued)

OTHER PUBLICATIONS

Koschwanez et al., In Vitro, In Vivo and Post Explantation Testing of Glucose-Detecting Biosensors: Current Methods and Recommendations, 2007, Biomaterials 28, pp. 3687-3703 (Year: 2007).*
(Continued)

*Primary Examiner* — Toan M Le
(74) *Attorney, Agent, or Firm* — Schwegman Lundberg & Woessner, P.A.

(57) ABSTRACT

Systems and methods are disclosed which provide for a "factory-calibrated" sensor. In doing so, the systems and methods include predictive prospective modeling of sensor behavior, and also include predictive modeling of physiology. With these two correction factors, a consistent determination of sensitivity can be achieved, thus achieving factory calibration.

13 Claims, 13 Drawing Sheets

Related U.S. Application Data continuation of application No. 16/407,055, filed on May 8, 2019, now Pat. No. 10,729,364, which is a continuation of application No. 15/394,327, filed on Dec. 29, 2016, now Pat. No. 10,362,975.

(60) Provisional application No. 62/272,975, filed on Dec. 30, 2015.

(51) Int. Cl.
*G01N 33/66* (2006.01)
*A61B 5/1486* (2006.01)

(56) References Cited

U.S. PATENT DOCUMENTS

| | | | |
|---|---|---|---|
| 6,477,395 | B2 | 11/2002 | Schulman et al. |
| 6,484,046 | B1 | 11/2002 | Say et al. |
| 6,512,939 | B1 | 1/2003 | Colvin et al. |
| 6,565,509 | B1 | 5/2003 | Say et al. |
| 6,579,690 | B1 | 6/2003 | Bonnecaze et al. |
| 9,149,220 | B2 | 10/2015 | Bohm et al. |
| 10,327,687 | B2 | 6/2019 | Ma et al. |
| 10,362,975 | B2 | 7/2019 | Ma et al. |
| 10,729,364 | B2 | 8/2020 | Ma et al. |
| 11,051,731 | B2 * | 7/2021 | Ma ................ A61B 5/1495 |
| 2005/0027463 | A1 | 2/2005 | Goode, Jr. et al. |
| 2006/0020187 | A1 | 1/2006 | Brister et al. |
| 2007/0027385 | A1 | 2/2007 | Brister et al. |
| 2007/0197890 | A1 | 8/2007 | Boock et al. |
| 2008/0108942 | A1 | 5/2008 | Brister et al. |
| 2008/0119703 | A1 | 5/2008 | Brister et al. |
| 2012/0166126 | A1 | 6/2012 | Engelhardt et al. |
| 2012/0197576 | A1 | 8/2012 | Feldman et al. |
| 2012/0262298 | A1 | 10/2012 | Bohm et al. |
| 2012/0265035 | A1 | 10/2012 | Bohm et al. |
| 2013/0325352 | A1 | 12/2013 | Greene et al. |
| 2014/0012511 | A1 | 1/2014 | Mensinger et al. |
| 2014/0114156 | A1 | 4/2014 | Bohm et al. |
| 2014/0273042 | A1 | 9/2014 | Saint |
| 2014/0278189 | A1 | 9/2014 | Vanslyke et al. |
| 2014/0378793 | A1 | 12/2014 | Kamath et al. |
| 2017/0188906 | A1 | 7/2017 | Ma et al. |
| 2017/0188907 | A1 | 7/2017 | Ma et al. |
| 2019/0261904 | A1 | 8/2019 | Ma et al. |

FOREIGN PATENT DOCUMENTS

| | | |
|---|---|---|
| JP | 2014514093 A | 6/2014 |
| JP | 2018532440 A | 11/2018 |

OTHER PUBLICATIONS

Hoss et al., Feasibility of Factory Calibration for Subcutaneous Glucose Sensors in Subjects with Diabetes, 2014, Journal of Diabetes Science and Technology, vol. 8(1), pp. 89-94 (Year: 2014).*
Extended European Search Report for Application No. 16882674.1 dated Jul. 18, 2019, 9 pages.
Hoss U., et al., "Continuous Glucose Monitoring in Subcutaneous Tissue Using Factory-Calibrated Sensors: A Pilot Study," Diabetes Technology & Therapeutics, 2010, vol. 12 (8), pp. 591-597.
Hoss U., et al., "Feasibility of Factory Calibration for Subcutaneous Glucose Sensors in Subjects with Diabetes," Journal of Diabetes Science and Technology, vol. 8(1), 2014, pp. 89-94.
International Preliminary Report on Patentability for Application No. PCT/US2016/069263 dated Jul. 12, 2018, 12 pages.
International Search Report and Written Opinion for Application No. PCT/US2016/069263 dated May 8, 2017, 14 pages.
Office Action from Australian Patent Application No. 2019213399, dated Oct. 23, 2020, 5 pages.
Office Action from Japanese Patent Application No. 2018-518433, dated Apr. 5, 2021, 4 pages.
Office Action from Japanese Patent Application No. 2018-518433, dated Sep. 14, 2020, 10 pages.

* cited by examiner

SYSTEM AND METHOD FOR FACTORY CALIBRATION OR REDUCED CALIBRATION OF AN INDWELLING SENSOR BASED ON SENSITIVITY PROFILE AND BASELINE MODEL OF SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/911,172, filed Jun. 24, 2020, which is a continuation of U.S. application Ser. No. 16/407,055, filed May 8, 2019, now U.S. Pat. No. 10,729,364, which is a continuation of U.S. application Ser. No. 15/394,327, filed Dec. 29, 2016, now U.S. Pat. No. 10,362,975, which claims the benefit of U.S. Provisional Application No. 62/272,975 filed Dec. 30, 2015. Each of the aforementioned applications is incorporated by reference herein in its entirety, and each is hereby expressly made a part of this specification.

TECHNICAL FIELD

Systems and methods for processing sensor data from continuous analyte sensors and for factory calibration of the sensors.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

Heretofore, a variety of glucose sensors have been developed for continuously measuring glucose values. Many implantable glucose sensors suffer from complications within the body and provide only short-term and less-than-accurate sensing of blood glucose. Similarly, transdermal sensors have run into problems in accurately sensing and reporting back glucose values continuously over extended periods of time.

In a continuous glucose monitor (CGM), after the sensor is implanted, it is calibrated, after which it provides substantially continuous sensor data to the sensor electronics. The sensor electronics convert the sensor data so that estimated analyte values can be continuously provided to the user. As used herein, the terms "substantially continuous," "continuously," etc., may refer to a data stream of individual measurements taken at time-spaced intervals, which may range from fractions of a second up to, for example, 1, 2, or 5 minutes or more. As the sensor electronics continue to receive sensor data, the sensor may be occasionally recalibrated to account for possible changes in sensor sensitivity and/or baseline (drift). Sensor sensitivity may refer to an amount of electrical current produced in the sensor by a predetermined amount of the measured analyte. Sensor baseline refers to a signal output by the sensor when no analyte is detected. Over time, sensitivity and baseline change due to a variety of factors, including cellular attack or migration of cells to the sensor, which can affect the ability of the analyte to reach the sensor.

One of the major hurdles facing CGM is the need the calibrate CGM sensors multiple times a day due to sensor inaccuracies caused by changes in membrane dynamics, electrochemistry, and physiology. While many sensors only require two calibrations a day, there is an increasing pressure from users for "factory-calibrated" sensors. A factory calibration implies that the sensors are calibrated "in" the factory, and there is no need for external user calibrations when the device is in use.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles meet the needs of the above in several ways. In particular, and in one implementation, systems and methods provide for a "factory-calibrated" sensor. In doing so, the systems and methods include predictive prospective modeling of sensor behavior, and also include predictive modeling of physiology. With these two correction factors, a consistent determination of sensitivity can be achieved, thus achieving factory calibration.

Without wishing to be bound by theory, it is believed that two major challenges have been met in systems and methods according to present principles in achieving factory calibration for continuous analyte, e.g., glucose, monitoring. A first challenge is that the sensitivity and background signals of the glucose sensors change as a function of time once the sensor is immersed in electrolyte. To a large extent, this time-varying behavior is replicable across sensors and can be described by mathematical models according to present principles that are defined by a small number of parameters. Based on the sensitivity and baseline signals predicted, e.g., in implementations according to present principles, one can calibrate glucose sensor signals to estimate blood glucose concentration in real time.

Secondly, substantial sensor-to-sensor variability exists in the inherent properties of glucose sensors and/or in how they are characterized on the bench, which has resulted in different in vivo time-courses of sensitivity and background signal profile's for each sensor. A test referred to as "cal check" has been used to determine an initial or in vitro value of sensitivity and the same has been found to be a reliable predictor of these in vivo properties. Systems and methods according to present principles have established a method to utilize cal check sensitivity information to adjust the mathematical models and to provide an adaptation for each individual sensor.

The factory calibration workflow, when combined with appropriate algorithms, e.g., the algorithm described in US PGP 2014/0278189, owned by the assignee of the current application and herein incorporated by reference in its entirety, attempts to parameterize a number of sensor performance metrics, e.g., initial/final sensitivity, drift performance, baseline shift, etc., as well as compartment effects, in order to prospectively model future performance. In one specific implementation, fourteen parameters have been identified and used.

According to present principles, this factory calibration workflow in one implementation includes two models that can be used together or separately—a sensitivity profile model and a baseline model. There are two exemplary versions of the sensitivity model, e.g., both a single parameter exponential model and a dual parameter exponential model, and one exemplary version of the baseline model. These two models have several parameter inputs such as initial sensitivity, final sensitivity, rate of exponential drift, drift rate due to membrane degradation, drift rate due to electrochemical break-in, initial and final magnitude of compartmental bias, drift rate of disappearing compartmental bias, and so on. Overall, the majority of these parameters may be fixed based on the sensor/membrane configuration and the data may be largely culled from cal check data and data from a long-term drift test conducted on a subset of sensors from the manufactured lot.

Without limiting the scope of the present embodiments as expressed by the claims that follow, prominent features of systems and methods according to present principles will be discussed briefly. After considering this discussion, and particularly after reading the section entitled "Detailed Description," one will understand how the features of the present embodiments provide the advantages described herein.

In a first aspect, a method of calibrating an analyte concentration sensor is provided, the sensor as a member of a manufactured lot of sensors, the lot of a given type of sensor, in which one or more operating parameters of the type of sensor of the lot have been determined, the determining of the operating parameters based on retrospective data, the operating parameters corresponding to at least a sensitivity of the sensor, the operating parameters representing in vivo values, the method including steps of: a. measuring one or more long term drift characteristics of sensitivity of a subset of sensors in the lot; b. for a subject sensor, measuring a value of an initial measurable parameter; c. correlating the measured value of the initial measurable parameter of the subject sensor to the measured one or more long term drift in vitro characteristics via a first set of coefficients; d. correlating at least a subset of the one or more determined in vivo operating parameters to the measured value of the initial measurable parameter via a second set of coefficients; and e. using the first and second set of coefficients to determine an estimated value of at least an in vivo final sensitivity of the subject sensor prospectively, where given a measured value of the initial measurable parameter of the subject sensor, an in vivo sensitivity value for the subject sensor can be estimated.

Implementations of the embodiments may include one or more of the following.

The measuring one or more long term drift characteristics of sensitivity of a subset of sensors in the lot may include measuring at least two long-term drift characteristics for sensors of the lot, the long-term drift characteristics including an initial long-term drift-test sensitivity and a final long-term drift-test sensitivity. The determining at least two drift characteristics of the sensor may further include determining a third drift characteristic that is a long-term drift-test rate of change sensitivity. The determining at least two drift characteristics of the sensor may further include determining at least two long term drift characteristics by disposing the sensor in a solution containing the analyte at a known concentration for a duration of time. The drift characteristics may be characterized by a sensitivity model defined by a set of sensitivity parameters. The sensitivity model may include an exponential function, such as a single exponential function or a dual exponential function. The set of sensitivity parameters may include $m_0$ or $m_F$ or both, and may further include $m_R$. The step of using the first and second set of coefficients to determine a predicted value of at least an in vivo final sensitivity of the subject sensor may further include using the first and second set of coefficients to determine a predicted value of an in vivo initial sensitivity of the subject sensor. The initial measurable parameter may be sensitivity. The initial measurable parameter may be a cal check sensitivity.

The determining cal check sensitivity of a sensor may further include: a. measuring an output signal of the analyte sensor at a plurality of values of an analyte concentration, and b. performing a linear regression procedure using the measured output signals and measured values of the analyte concentration. The initial measurable parameter may be a sensor membrane thickness. The determining one or more operating parameters may include using patient data to determine the in vivo operating parameters. The determining one or more operating parameters may include determining one or more operating parameters corresponding to a baseline signal and/or one or more operating parameters corresponding to sensitivity. The one or more operating parameters corresponding to sensitivity may include an operating parameter corresponding to a final value of sensitivity. The one or more operating parameters corresponding to sensitivity may include an operating parameter corresponding to an initial value of sensitivity. The set of sensitivity parameters and/or the set of baseline signal parameters may undergo a step of parameter fitting by minimizing a cost function to determine a set of best fit parameters. The cost function may be an absolute relative difference or a mean absolute relative difference. The parameter fitting may be unconstrained or constrained, e.g., where the constraint is based on the absolute value of the difference between each parameter and an initial value, added to the absolute relative difference, or where the constraint is based on the square of the absolute value of the difference. The set of sensitivity parameters may include $m_0$ and $m_F$, and may further include $m_R$. The set of baseline parameters may have a number of members between 5 and 15. The set of baseline parameters may include operating parameters that can be predicted by bench test or manufacturing parameters. The parameter fitting may include concatenating the sensitivity parameters and the baseline parameters into a single vector. The operating parameters may further correspond to a baseline model defined by a set of baseline parameters. The method may further include, when a subject sensor or sensor lot undergoes a step of determining a value of an initial measurable parameter, if the initial measurable parameter varies by more than a predetermined threshold from a predetermined value, or if a parameter derived from the initial measurable parameter varies by more than a predetermined threshold from a predetermined value, then performing a step of correcting the sensor calibration.

The initial measurable parameter may be a sensitivity, and the correcting may include altering the calibration such that a line on a graph of $m_0$ and $m_F$ versus initial cal check sensitivity, the line representing the relationship between $m_0$ and $m_F$ and the initial cal check sensitivity, is altered to intersect a line determined for a prior calculation at a point where the initial cal check sensitivity is zero.

The initial measurable parameter may be a sensitivity, and the correcting may include altering the calibration such that a line on a graph of $m_0$ and $m_F$ versus initial cal check sensitivity, the line representing the relationship between $m_0$ and $m_F$ and the initial cal check sensitivity, is altered to intersect a line determined for a prior calculation at a point where the value of $m_0$ and $m_F$, respectively, is zero.

In a second aspect, a method of calibrating an analyte concentration sensor is provided, the sensor as a member of a manufactured lot of sensors of a given type, the method including steps of: a. determining, receiving, or measuring an in vitro sensitivity of a first sensor; b. determining, receiving, or measuring at least one drift characteristic for a subset of sensors of the lot, the drift characteristic including at least a final drift-test sensitivity, the determined characteristic statistically representative of sensors in the lot; c. determining at least a first set of coefficients descriptive of a relationship between the initial in vitro sensitivity of the first sensor and the drift characteristic; d. determining at least a second set of coefficients descriptive of a relationship between a retrospective in vivo sensitivity and the determined first set of coefficients and the initial in vitro sensitivity of the first sensor; e. using the determined first or second sets of coefficients, or both, to calculate a predicted in vivo sensitivity of a second sensor given measured initial in vitro sensitivity of the second sensor; and f. storing the calculated predicted in vivo sensitivity of the second sensor for subsequent transmission to sensor electronics associated with the second sensor, or transmitting the calculated predicted in vivo sensitivity of the second sensor to sensor electronics associated with the second sensor.

Implementations of the embodiments may include one or more of the following.

The retrospective in vivo sensitivity may include at least a final in vivo sensitivity. The retrospective in vivo sensitivity may further include an initial in vivo sensitivity. The retrospective in vivo sensitivity may be determined using linear regression of prior data.

In a third aspect, a sensor electronics device is provided, including: a. a processor; b. a first input port configured to receive data from a sensor; c. a second input port configured to receive calibration data, the calibration data corresponding at least to a sensor sensitivity; and d. an output port configured to transmit sensor data to a mobile device.

Implementations of the embodiments may include one or more of the following.

The device may be a transmitter. The device may be mechanically configured to be physically coupled to a sensor. The output port may be configured for wired or wireless communications. The first input port may include at least two electrode contacts. The second input port and the output port may correspond to a common communications port. The second input port may be configured to receive a code, the code configured to provide calibration data for input to the sensor electronics device and/or to the mobile device. The second input port may be configured to receive the code by user input, network communications, NFC, RFID, a barcode, a mechanical means, or an optical means. The second input port may be configured to receive the code by user input, and the sensor electronics device may be configured to receive the user input from the mobile device. The sensor electronics device may further include a memory for storing a lookup table, and the second input port may be configured to receive a code that is convertible to at least a sensor sensitivity by use of the lookup table stored in the memory, the conversion occurring in the sensor electronics device or in the mobile device. The code may be further convertible to at least a sensor baseline signal by use of the lookup table stored in the memory.

In a fourth aspect, a kit for analyte concentration monitoring is provided, including: a. the sensor electronics device noted above; b. a sensor, where the sensor electronics device is mechanically configured to be physically coupled to the sensor; c. a calibration indicator, where the calibration indicator is configured to provide calibration data for input to the sensor electronics device and/or to the mobile device, the calibration data usable for calibrating the sensor such that the mobile device is configured to display sensor measurements in clinical units.

In a fifth aspect, a kit for analyte concentration monitoring is provided including: a. a sensor, where the sensor is mechanically configured to be physically coupled to the sensor electronics device; b. a calibration indicator, where the calibration indicator is configured to provide calibration data for input to the sensor electronics device and/or to the mobile device, the calibration data usable for calibrating the sensor such that the mobile device is configured to display sensor measurements in clinical units.

In a sixth aspect, a system for providing calibrated sensors is provided, where a lot of a given type of sensor has been manufactured, in which one or more operating parameters of the type of sensor of the lot have been determined, the determining of the operating parameters based on retrospective data, the operating parameters corresponding to at least a statistical representation of a sensitivity of sensors of the lot, the operating parameters representing in vivo values, the system including: a. a first device for manufacturing a lot of analyte concentration sensors, b. a second device for prospectively determining a calibration of a subject sensor from the lot, where the second device is configured to perform the steps of: i. measuring one or more long term drift characteristics of sensitivity of a subset of sensors in the manufactured lot; ii. for a subject sensor, measuring a value of an initial measurable parameter; iii. correlating the measured value of the initial measurable parameter of the subject sensor to the measured one or more long term drift characteristics using a first set of coefficients; iv. correlating at least a subset of the one or more determined in vivo operating parameters to the measured value of the initial measurable parameter via a second set of coefficients; and v. using the first and second set of coefficients to determine an estimated prospective value of at least an in vivo final sensitivity of the subject sensor, where, given a measured value of the initial measurable parameter of the subject sensor, an in vivo sensitivity value for the subject sensor is calculated.

Implementations of the embodiments may include one or more of the following.

The second device may be further configured to perform a step of creating a data file corresponding to a sensitivity profile, the sensitivity profile including or indicating at least the in vivo final sensitivity of the subject sensor. The second device may be further configured to perform a step of encoding the in vivo final sensitivity of the subject sensor in a calibration indicator, and is further configured to perform a step of packaging the subject sensor with the calibration indicator in a kit. The configuration of the second device to perform a step of encoding the in vivo final sensitivity of the subject sensor in a calibration indicator may further include configuring the second device to output a data file with the encoded sensitivity data. The calibration indicator may be embodied in a printed code whereby a user may input the printed code into a mobile device or sensor electronics to configure calibration. The printed code may be keyed to a lookup table stored in a sensor electronics device or in a mobile device, such that when the printed code is entered by the user, calibration information is retrieved from the lookup table and used to calibrate the sensor and sensor electronics. The calibration indicator may be embodied in an RFID or NFC device, where the RFID or NFC device may be swiped by the sensor electronics or a mobile device to transfer calibration data.

In a seventh aspect, a method of calibrating an analyte concentration sensor is provided, the sensor a member of a manufactured lot of sensors of a given type, the method including steps of: a. determining, receiving, or measuring an in vitro sensitivity of a first sensor; b. determining, receiving, or measuring at least one drift characteristic for a subset of sensors of the lot, the drift characteristic including at least a final drift-test sensitivity, the determined characteristic statistically representative of sensors in the lot; c. determining at least a first set of coefficients descriptive of a relationship between the initial in vitro sensitivity of the first sensor and the drift characteristic; d. determining at least a second set of coefficients descriptive of a relationship between a retrospective in vivo sensitivity and the determined first set of coefficients and the initial in vitro sensitivity of the first sensor; e. using the determined first or second sets of coefficients, or both, to calculate a sensitivity profile of a second sensor given a measured initial in vitro sensitivity of the second sensor; and f. storing the calculated predicted in vivo sensitivity of the second sensor for subsequent transmission to sensor electronics associated with the second sensor, or transmitting the calculated predicted in vivo sensitivity of the second sensor to sensor electronics associated with the second sensor.

In an eighth aspect, a system for calibrating an analyte concentration sensor is provided, the sensor as a member of a manufactured lot of sensors, the lot of a given type of sensor, in which one or more operating parameters of the type of sensor of the lot have been determined, the determining of the operating parameters based on retrospective data, the operating parameters corresponding to at least a sensitivity of the sensor, the operating parameters representing in vivo values, and in which, from a subset of sensors of the lot, one or more long term drift characteristics of sensitivity have been measured, the system including: a. a sensor calibration module configured to: i. for a subject sensor, measuring a value of an initial measurable parameter; ii. correlating the measured value of the initial measurable parameter of the subject sensor to the measured one or more long term drift characteristics via a first set of coefficients; iii. correlating at least a subset of the one or more retrospectively determined in vivo operating parameters to the measured value of the initial measurable parameter via a second set of coefficients; and iv. using the first and second set of coefficients to determine an estimated value of at least an in vivo final sensitivity of the subject sensor prospectively, where given a measured value of the initial measurable parameter of the subject sensor, an in vivo sensitivity value for the subject sensor can be estimated; b. a coding module configured to encode the in vivo final sensitivity of the subject sensor as a calibration indicator; and c. a packaging module configured to package the calibration indicator and the subject sensor in a kit.

In a ninth aspect, a downloadable application is provided, configured for running on a mobile device, the application performing a method for receiving and displaying calibrated analyte concentration data, the method including steps of: a. receiving a code, the code keyed to a sensitivity value; b. receiving a sensor signal, the sensor signal in current or counts; c. using the code or the sensitivity value, and the sensor signal, to calculate a calibrated analyte concentration value; and d. displaying the calculated value; e. where the code is keyed to a sensitivity value by a lookup table stored in the mobile device or in sensor electronics in data communication with the sensor and mobile device, or where the code includes the sensitivity value; and f. where the sensitivity value includes at least a final sensitivity value and an initial sensitivity value.

In a tenth aspect, a method of calibrating an analyte concentration sensor is provided, the sensor as a member of a manufactured lot of sensors, the lot of a given type of sensor, in which one or more operating parameters of the type of sensor of the lot have been determined, the determining of the operating parameters based on retrospective data, the operating parameters corresponding to at least a sensitivity of the sensor, the operating parameters representing in vivo values, the method including steps of: a. for a subject sensor, measuring a value of an initial measurable parameter; b. correlating the measured value of the initial measurable parameter of the subject sensor to the one or more determined operating parameters via at least one coefficient; and c. using the coefficient to determine an estimated value of at least an in vivo final sensitivity of the subject sensor prospectively, wherein given a measured value of the initial measurable parameter of the subject sensor, an in vivo sensitivity value for the subject sensor can be estimated.

In one exemplary implementation, the method further includes measuring one or more long-term drift characteristics of sensitivity of a subset of sensors in the lot, and the correlating further correlates the measured value of the initial measurable parameter to the measured one or more long-term drift characteristics via at least another coefficient, and the coefficient is used with the another coefficient to determine the estimated value of at least the in vivo final sensitivity of the subject sensor prospectively.

In an eleventh aspect, a method of calibrating an analyte concentration sensor is provided, the sensor as a member of a manufactured lot of sensors, the lot of a given type of sensor, in which one or more in vivo operating parameters of the type of sensor of the lot have been determined, the method including steps of: a. for a subject sensor, measuring a value of an initial measurable parameter; b. correlating the measured value of the initial measurable parameter of the subject sensor to the one or more in vivo operating parameters via at least one coefficient; and c. using the coefficient to determine an estimated value of at least an in vivo final sensitivity of the subject sensor prospectively, wherein given a measured value of the initial measurable parameter of the subject sensor, an in vivo sensitivity value for the subject sensor can be estimated.

In further aspects and embodiments, the above method features of the various aspects are formulated in terms of a system as in various aspects, configured to carry out the method features. Any of the features of an embodiment of any of the aspects, including but not limited to any embodiments of any of the first through eleventh aspects referred to above, is applicable to all other aspects and embodiments identified herein, including but not limited to any embodiments of any of the first through eleventh aspects referred to above. Moreover, any of the features of an embodiment of the various aspects, including but not limited to any embodiments of any of the first through eleventh aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through eleventh aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through eleventh aspects referred to above.

Advantages of the embodiments may include, in certain embodiments, one or more of the following. The challenges of achieving factory calibration for continuous glucose monitoring are in some implementations effectively solved. For example, the sensitivity and background signals of the glucose sensors change as a function of time once the sensor is immersed in electrolyte, but this time-varying behavior can be described by mathematical models that are defined by a small number of parameters. Based on the sensitivity and baseline signals predicted by systems and methods according to present principles, calibration can occur of glucose sensor signals to estimate blood glucose concentration in real time. Systems and methods according to present principles have established ways to utilize measurable parameters such as cal check sensitivity information (described below) to correct the mathematical models and allow an adapted calibration for each individual sensor.

Other advantages will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The present embodiments now will be discussed in detail with an emphasis on highlighting the advantageous features. These embodiments depict the novel and nonobvious sensor signal processing and calibration systems and methods shown in the accompanying drawings, which are for illustrative purposes only and are not to scale, instead emphasizing the principles of the disclosure. These drawings include the following figures, in which like numerals indicate like parts.

Like reference numerals refer to like elements throughout. Elements are not to scale unless otherwise noted.

DETAILED DESCRIPTION

Figure 1:
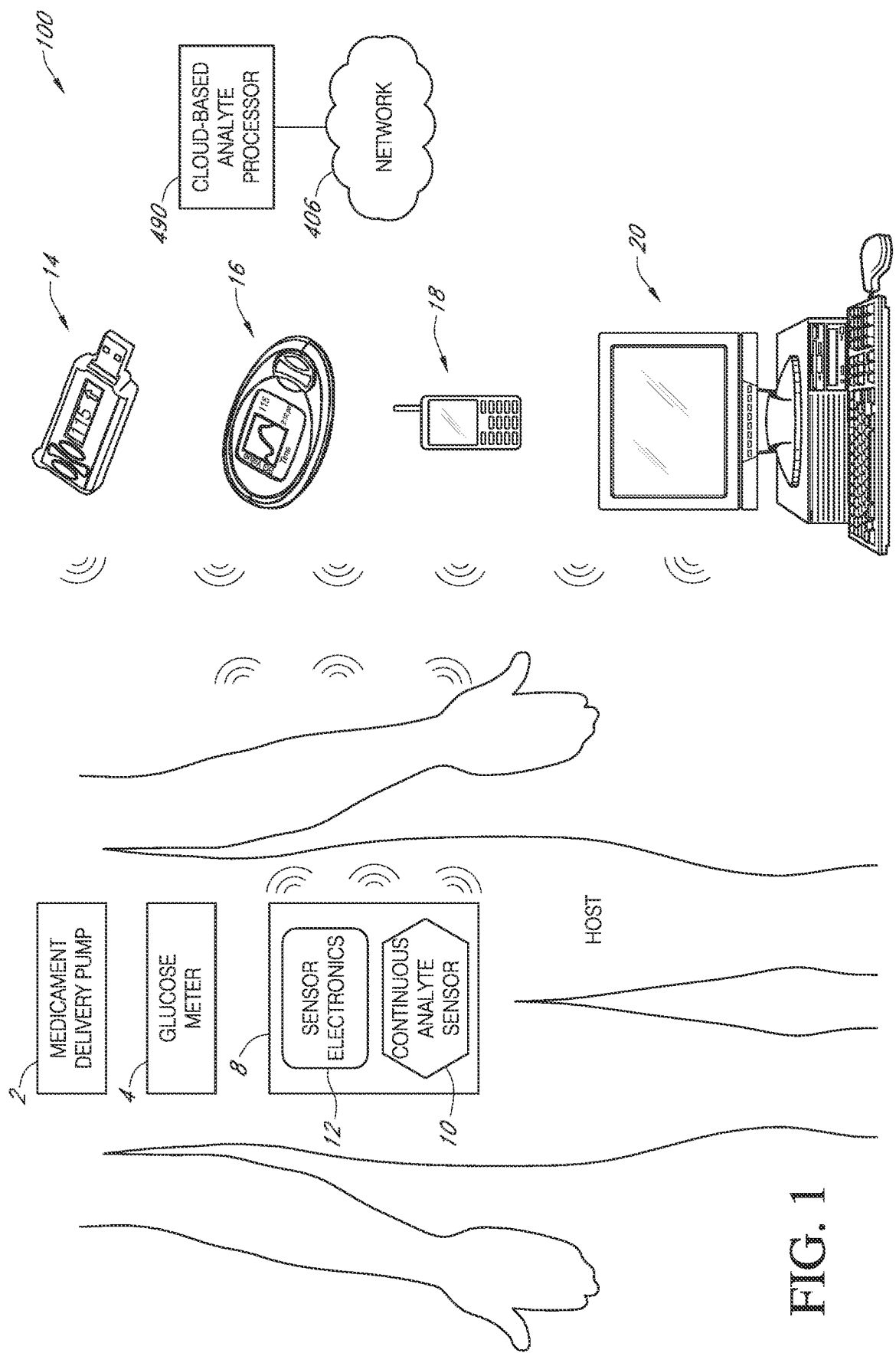
FIG. 1 is a schematic view of a continuous analyte sensor system attached to a host and communicating with a plurality of example devices.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Definitions

In order to facilitate an understanding of the preferred embodiments, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the substance for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "raw data stream" and "data stream" as used herein are broad terms and are to be given their ordinary and customary meaning to a person of ordinary skill in the art (and are not to be limited to a special or customized meaning), and furthermore refer without limitation to an analog or digital signal directly related to the measured glucose from the glucose sensor. In one example, the raw data stream is digital data in "counts" converted by an A/D converter from an analog signal (e.g., voltage or amps) and includes one or more data points representative of a glucose concentration. The terms broadly encompass a plurality of time spaced data points from a substantially continuous glucose sensor, which comprises individual measurements taken at time intervals ranging from fractions of a second up to, e.g., 1, 2, or 5 minutes or longer. In another example, the raw data stream includes an integrated digital value, wherein the data includes one or more data points representative of the glucose sensor signal averaged over a time period.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data, with or without utilizing reference data in real time. In some embodiments, namely, in continuous analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, including by use of a sensitivity, to provide a meaningful value to a user.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified. A "lot" of sensors generally refers to a group of sensors that are manufactured on or around the same day and using the same processes and tools/materials.

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

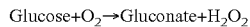

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, calculating, deriving, establishing and/or the like. Determining may also include ascertaining that a parameter matches a predetermined criterion, including that a threshold has been met, passed, exceeded, and so on.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte (or glucose) sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for the continuous analyte sensor, for example a self-monitoring blood glucose meter (SMBG) can be used as a reference for a continuous glucose sensor for comparison, calibration, and the like.

The term "sensing membrane" as used herein is a broad term and is to be given its ordinary and customary meaning to a person of ordinary skill in the art (and is not to be limited to a special or customized meaning), and furthermore refers without limitation to a permeable or semi-permeable membrane that can be comprised of two or more domains and is typically constructed of materials of a few microns thickness or more, which are permeable to oxygen and may or may not be permeable to glucose. In one example, the sensing membrane comprises an immobilized glucose oxidase enzyme, which enables an electrochemical reaction to occur to measure a concentration of glucose.

The term "physiologically feasible" as used herein is a broad term and is to be given its ordinary and customary meaning to a person of ordinary skill in the art (and is not to be limited to a special or customized meaning), and furthermore refers without limitation to the physiological parameters obtained from continuous studies of glucose data in humans and/or animals. For example, a maximal sustained rate of change of glucose in humans of about 4 to 5 mg/dL/min and a maximum acceleration of the rate of change of about 0.1 to 0.2 mg/dL/min$^2$ are deemed physiologically feasible limits. Values outside of these limits would be considered non-physiological and likely a result of signal error, for example. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (e.g., about 20 to 30 minutes) is a straight line, which can be used to set physiological limits.

The term "frequency content" as used herein is a broad term and is to be given its ordinary and customary meaning to a person of ordinary skill in the art (and is not to be limited to a special or customized meaning), and furthermore refers without limitation to the spectral density, including the frequencies contained within a signal and their power.

The term "linear regression" as used herein is a broad term and is to be given its ordinary and customary meaning to a person of ordinary skill in the art (and is not to be limited to a special or customized meaning), and furthermore refers without limitation to finding a line in which a set of data has a minimal measurement from that line. Byproducts of this algorithm include a slope, a y-intercept, and an R-Squared value that determine how well the measurement data fits the line.

The term "non-linear regression" as used herein is a broad term and is to be given its ordinary and customary meaning to a person of ordinary skill in the art (and is not to be limited to a special or customized meaning), and furthermore refers without limitation to fitting a set of data to describe the relationship between a response variable and one or more explanatory variables in a non-linear fashion.

The term "mean" as used herein is a broad term and is to be given its ordinary and customary meaning to a person of ordinary skill in the art (and is not to be limited to a special or customized meaning), and furthermore refers without limitation to the sum of the observations divided by the number of observations.

The term "non-recursive filter" as used herein is a broad term and is to be given its ordinary and customary meaning to a person of ordinary skill in the art (and is not to be limited to a special or customized meaning), and furthermore refers without limitation to an equation that uses moving averages of inputs as outputs.

The terms "recursive filter" and "auto-regressive algorithm" as used herein are broad terms and are to be given their ordinary and customary meaning to a person of ordinary skill in the art (and are not to be limited to a special or customized meaning), and furthermore refer without limitation to an equation in which averages of previous outputs are part of the next filtered output. More particularly, the generation of a series of observations whereby the value of each observation is partly dependent on the values of those that have immediately preceded it. One example is a regression structure in which lagged response values assume the role of the independent variables for calculating the subsequent response.

The term "variation" as used herein is a broad term and is to be given its ordinary and customary meaning to a person of ordinary skill in the art (and is not to be limited to a special or customized meaning), and furthermore refers without limitation to a divergence or amount of change from a point, line, or set of data. In one embodiment, estimated analyte values can have a variation including a range of values outside of the estimated analyte values that represent a range of possibilities based on known physiological patterns, for example.

The terms "physiological parameters" and "physiological boundaries" as used herein are broad terms and are to be given their ordinary and customary meaning to a person of ordinary skill in the art (and are not to be limited to a special or customized meaning), and furthermore refer without limitation to the parameters obtained from continuous studies of physiological data in humans and/or animals. For example, a maximal sustained rate of change of glucose in humans of about 4 to 5 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (for example, about 20 to 30 minutes) is a straight line, which can be used to set physiological limits. These terms are broad enough to include physiological parameters for any analyte.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values.

The terms "sensor data," as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signals directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The terms broadly encompass a plurality of time spaced data points from a sensor, such as from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period.

Sensor data may include calibrated data, smoothed data, filtered data, transformed data, and/or any other data associated with a sensor.

The term "matched data pair" or "data pair" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "sensor electronics," as used herein, is a broad term, and is to be given its ordinary and customary meaning to a person of ordinary skill in the art (and is not to be limited to a special or customized meaning), and refers without limitation to the components (for example, hardware and/or software) of a device configured to process data.

The term "calibration set" as used herein is a broad term, and is to be given its ordinary and customary meaning to a person of ordinary skill in the art (and is not to be limited to a special or customized meaning), and refers without limitation to a set of data comprising information useful for calibration. In some embodiments, the calibration set is formed from one or more matched data pairs, which are used to determine the relationship between the reference data and the sensor data; however other data derived pre-implant, externally or internally may also be used.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., $H_2O_2$) associated with the measured analyte (e.g., glucose). For example, in one embodiment, a sensor has a sensitivity of from about 1 to about 300 pico Amps of current for every 1 mg/dL of glucose analyte.

The terms "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

Other definitions will be provided within the description below, and in some cases from the context of the term's usage.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview/General Description of System

Conventional in vivo continuous analyte sensing technology has typically relied on reference measurements performed during a sensor session for calibration of the continuous analyte sensor. The reference measurements are matched with substantially time corresponding sensor data to create matched data pairs. Regression is then performed on the matched data pairs (e.g., by using least squares regression) to generate a conversion function that defines a relationship between a sensor signal and an estimated glucose concentration.

In critical care settings, calibration of continuous analyte sensors is often performed by using, as a reference, a calibration solution with a known concentration of the analyte. This calibration procedure can be cumbersome, as a calibration bag, separate from (and an addition to) an IV (intravenous) bag, is typically used. In the ambulatory setting, calibration of continuous analyte sensors has traditionally been performed by capillary blood glucose measurements (e.g., a finger stick glucose test), through which reference data is obtained and entered into the continuous analyte sensor system. This calibration procedure typically involves frequent finger stick measurements, which can be inconvenient and painful.

Heretofore, systems and methods for in vitro calibration of a continuous analyte sensor by the manufacturer (e.g., factory calibration), without reliance on periodic recalibration, have for the most part been inadequate with respect to high levels of sensor accuracy required for glycemic management. Part of this can be attributed to changes in sensor properties (e.g., sensor sensitivity) that can occur during sensor use. Thus, calibration of continuous analyte sensors has typically involved periodic inputs of reference data, whether they are associated with a calibration solution or with a finger stick measurement. This can be very burdensome to the user during everyday life as well as to patients in the ambulatory setting or the hospital staff in the critical care setting.

Described herein are systems and methods for calibrating continuous analyte sensors that are capable of achieving high levels of accuracy, without (or with reduced) reliance on reference data from a reference analyte monitor (e.g., from a blood glucose meter).

The following description and examples described the present embodiments with reference to the drawings. In the drawings, reference numbers label elements of the present embodiments. These reference numbers are reproduced below in connection with the discussion of the corresponding drawing features.

Sensor System

FIG. 1 depicts an example system 100, in accordance with some example implementations. The system 100 includes a continuous analyte sensor system 8 including sensor electronics 12 and a continuous analyte sensor 10. The system 100 may include other devices and/or sensors, such as medicament delivery pump 2 and glucose meter 4. The continuous analyte sensor 10 may be physically connected to sensor electronics 12 and may be integral with (e.g., non-releasably attached to) or releasably attachable to the continuous analyte sensor 10. The sensor electronics 12, medicament delivery pump 2, and/or glucose meter 4 may couple with one or more devices, such as display devices 14, 16, 18, and/or 20.

In some example implementations, the system 100 may include a cloud-based analyte processor 490 configured to analyze analyte data (and/or other patient-related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame. A full discussion of using a cloud-based analyte processing system may be found in U.S. patent application Ser. No. 13/788,375, entitled "Cloud-Based Processing of Analyte Data" and filed on Mar. 7, 2013, herein incorporated by reference in its entirety. In some implementations, one or more steps of the factory calibration algorithm can be performed in the cloud.

In some example implementations, the sensor electronics 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics 12 may include hardware, firmware, software, or a combination thereof, to provide measurement of levels of the analyte via a continuous analyte sensor, such as a continuous glucose sensor. An example implementation of the sensor electronics 12 is described further below with respect to FIG. 2.

In one implementation, the factory calibration algorithms described herein may be performed by the sensor electronics.

The sensor electronics 12 may, as noted, couple (e.g., wirelessly and the like) with one or more devices, such as display devices 14, 16, 18, and/or 20. The display devices 14, 16, 18, and/or 20 may be configured for presenting information (and/or alarming), such as sensor information transmitted by the sensor electronics 12 for display at the display devices 14, 16, 18, and/or 20.

The display devices may include a relatively small, key fob-like display device 14, a relatively large, hand-held display device 16, a cellular phone 18 (e.g., a smart phone, a tablet, and the like), a computer 20, and/or any other user equipment configured to at least present information (e.g., medicament delivery information, discrete self-monitoring glucose readings, heart rate monitor, caloric intake monitor, and the like).

In one implementation, the factory calibration algorithms described herein may be performed at least in part by the display devices.

In some example implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device 16) and may be configured to display certain types of displayable sensor information, such as a numerical value, and an arrow, or a color code.

In some example implementations, the relatively large, hand-held display device 16 may comprise a hand-held receiver device, a palm-top computer, and/or the like. This large display device may include a relatively larger display (e.g., larger than the small display device 14) and may be configured to display information, such as a graphical representation of the continuous sensor data including current and historic sensor data output by sensor system 8.

In some example implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may comprise any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the disclosure herein refers to some implementations that include a continuous analyte sensor 10 comprising a glucose sensor, the continuous analyte sensor 10 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

Figure 2:
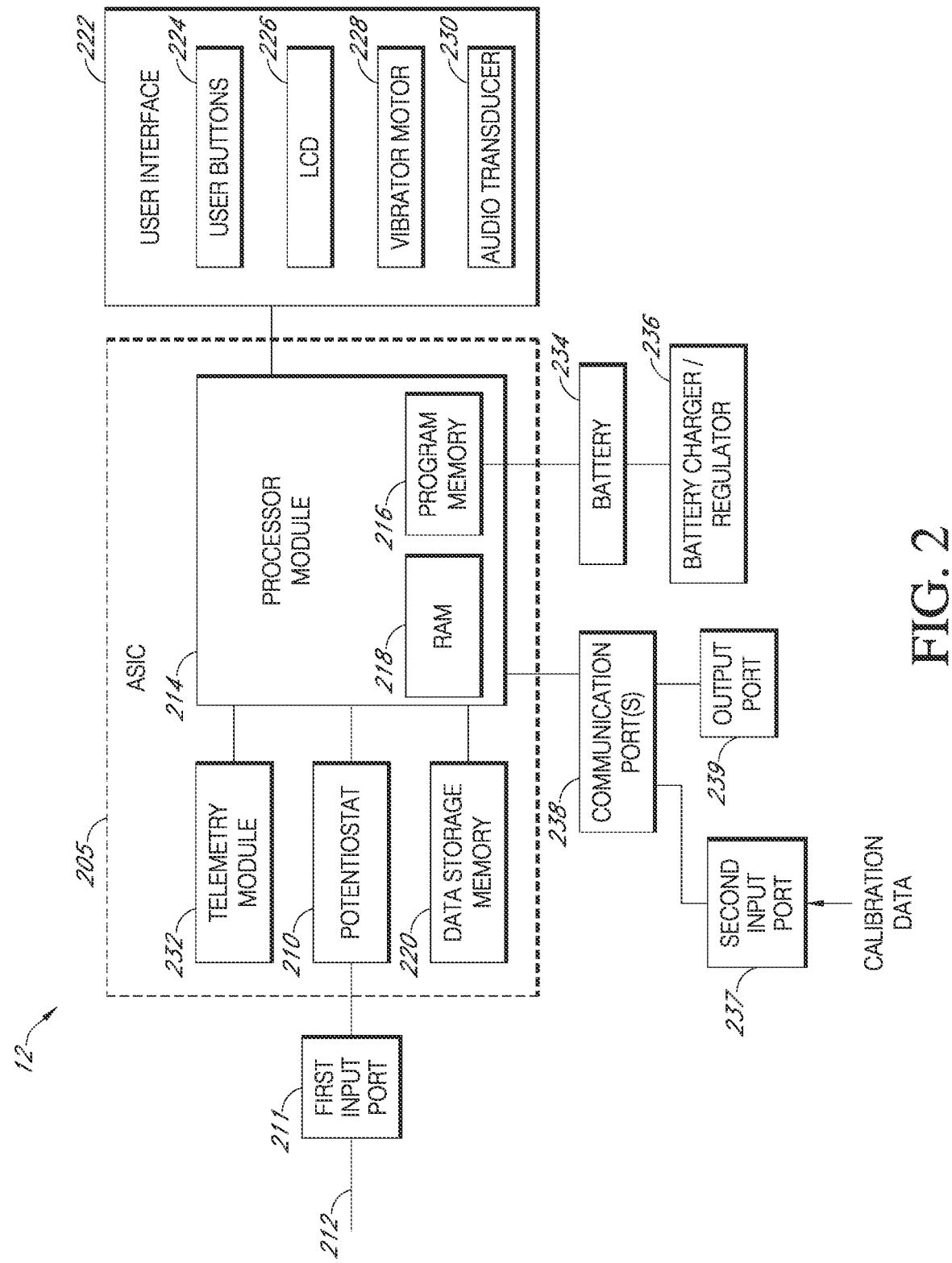
FIG. 2 is a block diagram that illustrates electronics associated with the sensor system of FIG. 1.

FIG. 2 depicts an example of sensor electronics 12, in accordance with some example implementations. The sensor electronics 12 may include sensor electronics that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information such as may be determined by factory calibration algorithms as disclosed herein, smoothing and/or filtering algorithms of sensor data, and/or the like.

In some embodiments, a processor module 214 is configured to achieve a substantial portion, if not all, of the data processing, including data processing pertaining to factory calibration. Processor module 214 may be integral to sensor electronics 12 and/or may be located remotely, such as in one or more of devices 14, 16, 18, and/or 20 and/or cloud 490. In some embodiments, processor module 214 may comprise a plurality of smaller subcomponents or submodules. For example, processor module 214 may include an alert module (not shown) or prediction module (not shown), or any other suitable module that may be utilized to efficiently process data. When processor module 214 is made up of a plurality of submodules, the submodules may be located within processor module 214, including within the sensor electronics 12 or other associated devices (e.g., 14, 16, 18, 20 and/or 490). For example, in some embodiments, processor module 214 may be located at least partially within a cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 14, 16, 18, and/or 20, to enable calibration of the sensor data from sensor 12. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms. The processor module 214 may further be configured to store and use calibration information determined from a factory calibration, as described below.

In some example implementations, the sensor electronics 12 may comprise an application-specific integrated circuit (ASIC) 205 coupled to a user interface 222. The ASIC 205 may further include a potentiostat 210, a telemetry module 232 for transmitting data from the sensor electronics 12 to one or more devices, such as devices 14, 16, 18, and/or 20, and/or other components for signal processing and data storage (e.g., processor module 214 and data storage memory 220). Although FIG. 2 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted in FIG. 2, through a first input port 211 for sensor data the potentiostat 210 is coupled to a continuous analyte sensor 10, such as a glucose sensor to generate sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels depending on the number of working electrodes at the continuous analyte sensor 10.

In some example implementations, the potentiostat 210 may include a resistor that translates a current value from the sensor 10 into a voltage value, while in some example implementations, a current-to-frequency converter (not shown) may also be configured to integrate continuously a measured current value from the sensor 10 using, for example, a charge-counting device. In some example implementations, an analog-to-digital converter (not shown) may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 12 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although Bluetooth technology may also be implemented in a combination of the telemetry module 232 and the processor module 214.

The processor module 214 may control the processing performed by the sensor electronics 12. For example, the processor module 214 may be configured to process data (e.g., counts), from the sensor, filter the data, calibrate the data, perform fail-safe checking, and/or the like.

In some example implementations, the processor module 214 may comprise a digital filter, such as for example an infinite impulse response (IIR) or a finite impulse response (FIR) filter. This digital filter may smooth a raw data stream received from sensor 10. Generally, digital filters are programmed to filter data sampled at a predetermined time interval (also referred to as a sample rate). In some example implementations, such as when the potentiostat 210 is configured to measure the analyte (e.g., glucose and/or the like) at discrete time intervals, these time intervals determine the sampling rate of the digital filter. In some example implementations, the potentiostat 210 may be configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator (not shown) configured to generate data packages for transmission to devices, such as the display devices 14, 16, 18, and/or 20. Furthermore, the processor module 214 may generate data packets for transmission to these outside sources via telemetry module 232. In some example implementations, the data packages may, as noted, be customizable for each display device, and/or may include any available data, such as a time stamp, displayable sensor information, transformed sensor data, an identifier code for the sensor and/or sensor electronics 12, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/ functions described herein. For example, the program code may configure processor module 214 to process data streams or counts, filter, perform the calibration methods described below, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 2, 3, 4, 5, 6, 7, 8, 9, 10, 11, 12, 13, 14, 15, 20, and/or 30 (or more days) of continuous analyte sensor data received from sensor 10. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information such as from factory calibration), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., acknowledged or turned off) by pressing one or more buttons 224 on the sensor electronics 12 and/or by signaling the sensor electronics 12 using a button or selection on a display device (e.g., key fob, cell phone, and/or the like).

Although audio and vibratory alarms are described with respect to FIG. 2, other alarming mechanisms may be used as well. For example, in some example implementations, a tactile alarm is provided including a poking mechanism configured to "poke" or physically contact the patient in response to one or more alarm conditions.

The battery 234 may be operatively connected to the processor module 214 (and possibly other components of the sensor electronics 12) and provide the necessary power for the sensor electronics 12. In some example implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery is rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics 12 to be fully charged without overcharging other cells or batteries. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 12. The communication port, for example, may comprise a serial (e.g., universal serial bus or "USB") communication port, and allow for communicating with another computer system (e.g., PC, personal digital assistant or "PDA," server, or the like). In some example implementations, the sensor electronics 12 is able to transmit historical data to a PC or other computing device (e.g., an analyte processor as disclosed herein) for retrospective analysis by a patient and/or physician. As another example of data transmission, factory information may also be sent to the algorithm from the sensor or from a cloud data source.

The one or more communication ports 238 may further include a second input port 237 in which calibration data may be received, and an output port 239 which may be employed to transmit calibrated data, or data to be calibrated, to a receiver or mobile device. FIG. 2 illustrates these aspects schematically. It will be understood that the ports may be separated physically, but in alternative implementations a single communication port may provide the functions of both the second input port and the output port.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 12 (e.g., via processor module 214) may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2, a variety of configurations may be used as well. For example, one or more memories may be used to provide storage space to support data processing and storage requirements at sensor electronics 12.

Calibration

In some cases calibration of an analyte sensor may use a priori calibration information. As used herein, a priori information includes information obtained prior to a particular calibration. For example, from previous calibrations of a particular sensor session (e.g., feedback from a previous calibration(s)), information obtained prior to sensor insertion (e.g., factory information from in vitro testing or data obtained from previously implanted analyte concentration sensors, such as sensors of the same manufacturing lot of the sensor and/or sensors from one or more different lots), prior in vivo testing of a similar sensor on the same host, and/or prior in vivo testing of similar sensors on different hosts. Calibration information includes information useful in calibrating a continuous glucose sensor, such as, but not limited to: sensitivity (m), change in sensitivity (dm/dt), which may also be referred to drift in sensitivity), acceleration of change of sensitivity ($d^2m/dt^2$), baseline/intercept (b), change in baseline (db/dt), rate of change of baseline ($d^2b/dt^2$), baseline and/or sensitivity profiles (i.e., change over a time period) associated with the sensor; linearity, response time, relationships between properties of the sensor (e.g., relationships between sensitivity and baseline, or relationships between particular stimulus signal output (e.g., output indicative of an impedance, capacitance or other electrical or chemical property of the sensor) and sensor sensitivity or temperature (e.g., determined from prior in vivo and/or in vitro studies) such as described in U.S. Patent Publication 2012-0265035-A1, which is incorporated herein by reference in its entirety; sensor data obtained from previously implanted analyte concentration sensors; calibration code(s) associated with a sensor being calibrated; patient specific relationships between sensor and sensitivity, baseline, drift, impedance, impedance/temperature relationship (e.g., determined from prior studies of the patient or other patients having common characteristics with the patient), site of sensor implantation (abdomen, arm, etc.) and/or specific relationships (different sites may have different vascular density). Distribution information includes ranges, distribution functions, distribution parameters (mean, standard deviation, skewness, etc.), generalized functions, statistical distributions, profiles, or the like that represent a plurality of possible values for calibration information. Taken together, a priori calibration distribution information includes range(s) or distribution(s) of values (e.g., describing their associated probabilities, probability density functions, likelihoods, or frequency of occurrence) provided prior to a particular calibration process useful for calibration of the sensor (e.g., sensor data).

For example, in some embodiments, a priori calibration distribution information includes probability distributions for sensitivity (m) or sensitivity-related information and baseline (b) or baseline-related information based on e.g., sensor type. As described above, the prior distribution of sensitivity and/or baseline may be factory-derived (e.g., from in vitro or in vivo testing of representative sensors) or derived from previous calibrations.

Figure 3:
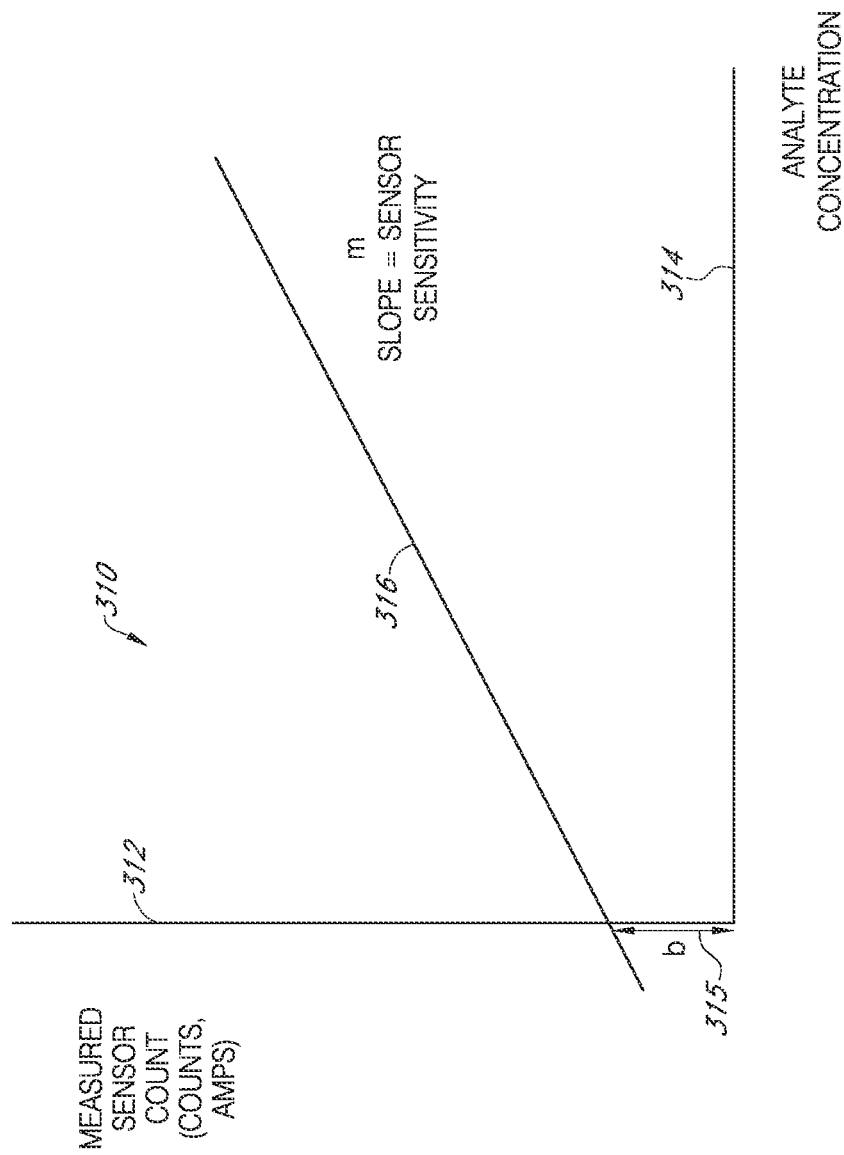
FIG. 3 depicts a graph illustrating a linear relationship between the measured sensor count and analyte concentration.

As noted above, an analyte sensor generally includes an electrode to monitor a current change in either a co-reactant or a product to determine analyte concentration, e.g., glucose concentration. In one example, the sensor data comprises digital data in "counts" converted by an A/D converter from an analog signal (e.g., voltage or amps). Calibration is the process of determining the relationship between the measured sensor signal in counts and the analyte concentration in clinical units. For example, calibration allows a given sensor measurement in counts to be associated with a measured analyte concentration value, e.g., in milligrams per deciliter. Referring to the graph 310 of FIG. 3, this relationship is generally a linear one, of the form y=mx+b, where 'y' is the sensor signal in counts or pico-amps (y-axis 312), 'x' is the clinical value of the analyte concentration (axis 314), and 'm' is the sensor sensitivity, having units of [counts/(mg/dL)] or [pA/(mg/dL)]. A line 316 is illustrated whose slope is termed the sensor sensitivity. 'b' (see line segment 315) is the baseline sensor signal, which can be taken into account, or for advanced sensors, can generally be reduced to zero or nearly zero. In some implementations a constant background signal is seen, and such are modeled by y=m(x+d), where d is a glucose offset between the sensor site and the blood glucose. In any event, once the line 316 has been determined, the system can convert a measured number of counts (or amps, e.g., picoamps, as described above) to a clinical value of the analyte concentration.

A more generalized form of the linear equation is provided below, and it will be understood that nonlinear relationships may also be used in factory calibrations according to present principles.

Figure 5:
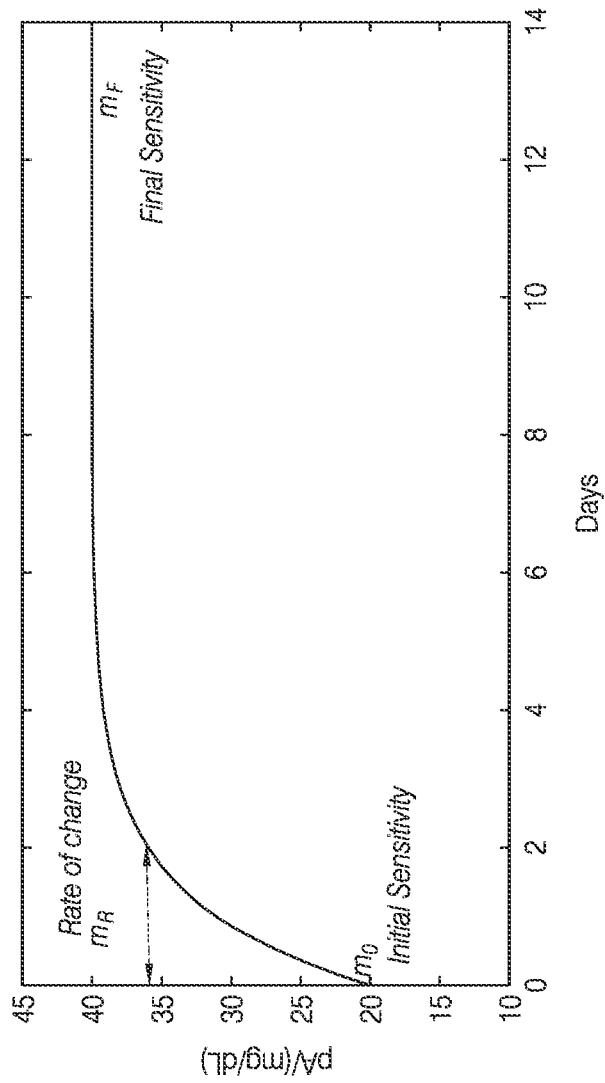
FIG. 5 illustrates an exemplary change of sensitivity over time, in particular showing a single exponential model.

In one specific situation, values of m and b vary from sensor to sensor and require determination. In addition, the slope value m is not always constant. For example, and referring to FIG. 5, the value m can be seen to change from an initial sensitivity value $m_0$ to a final sensitivity value $m_F$ over the course of time within a session. Its rate of change is seen to be greatest in the first few days of use, and this rate of change is termed $m_R$.

The slope is a function of in vivo time for a number of reasons. Particularly for initial changes in calibration, such are often due to the sensor membrane "settling in" and achieving equilibrium with the in vivo environment. Sensors are generally initially calibrated in vitro or on the bench, and efforts are made to make the in vitro environment as close as possible to the in vivo one, but differences are still apparent, and the in vivo environment itself changes from user to user. In addition, sensors may vary due to differences in the micro-environment each sensor faces during manufacturing and testing, and sterilization or shelf-life/storage conditions. Calibration changes that occur later in the session are often due to changes in the tissue surrounding the sensor, e.g., a buildup of biofilm on the sensor.

Whatever the cause, certain effects of variability have been measured and determined. For example, it is known that variability in the final sensitivity $m_F$ is the largest contributor to overall sensor inaccuracy. Similarly, it is known that variability in the initial sensitivity $m_0$ and physiology are the largest contributors to inaccuracy of sensors on the first day.

Thus, while calibration is critical to effective use of such sensors, user efforts in performing such calibrations are desired to be minimized. Present systems and methods according to present principles are directed in part to ways of reducing or eliminating such required calibrations.

In particular, and as noted above, one exemplary factory calibration workflow attempts to parameterize a number of sensor operating parameters (e.g. initial/final sensitivity, drift performance, baseline shift, etc.) and compartment effects in order to prospectively model future sensor behavior. This factory calibration workflow includes in one implementation two models—a sensitivity profile model, which may be single parameter or dual parameter, and a baseline model. These two models have several operating parameter inputs such as initial sensitivity, final sensitivity, rate of exponential drift, drift rate due to membrane degradation, drift rate due to electrochemical break-in, initial and final magnitude of compartmental bias, and drift rate of disappearing compartmental bias. Overall, the majority of these operating parameters are fixed based on the sensor/membrane configuration and data culled largely from clinical studies.

To obtain a 'key' or 'index' value to a specific sensor, and in particular to advantageously obtain a relationship between initial measurable sensor parameters and the desired "end result" in vivo sensitivity values, a "cal check" test and a long-term drift test may be performed, where the cal check test data is obtained non-destructively and corresponds generally to the signal output of the sensor as a function of a plurality of input analyte concentrations. That is, in the cal check test, a sensor is placed in test solutions of analytes having varying analyte concentrations, and the corresponding output signal is measured. The "calibration check" or "cal check" test may be performed to demonstrate sensor linearity to a high glucose concentration level (e.g., 400 mg/dL, 500 mg/dL, or 600 mg/dL). This is done by placing the sensor in buffer solutions of increasing glucose concentrations (e.g., in steps of 100 mg/dL). Calibration check is also performed to demonstrate sensor linearity at a low oxygen concentration (e.g., pO2 of 0.25 mg/L) and to demonstrate a 95% response time that is within an accepted limit (e.g., within 5 minutes).

Using the "cal check" test, one can determine an in vitro initial sensitivity or slope by measuring several such outputs as a function of analyte concentration, and performing a linear regression. However, any test may be employed, so long as a characteristic or other such index of a sensor or initial measurable parameter of a sensor is determined, where the characteristic or index or initial measurable parameter of the sensor can be later used as an independent variable to determine a prospective value of one or more in vivo operating parameters, e.g., an initial and/or final value of sensitivity, as will be described in greater detail below. In many cases, the cal check sensor sensitivity or slope is a preferred such initial measurable parameter, although other initial measurable parameters may also be employed, e.g., initial membrane thickness, or the like. Generally, but not always, appropriate initial measurable parameters include those measurable in vitro.

Figure 4:
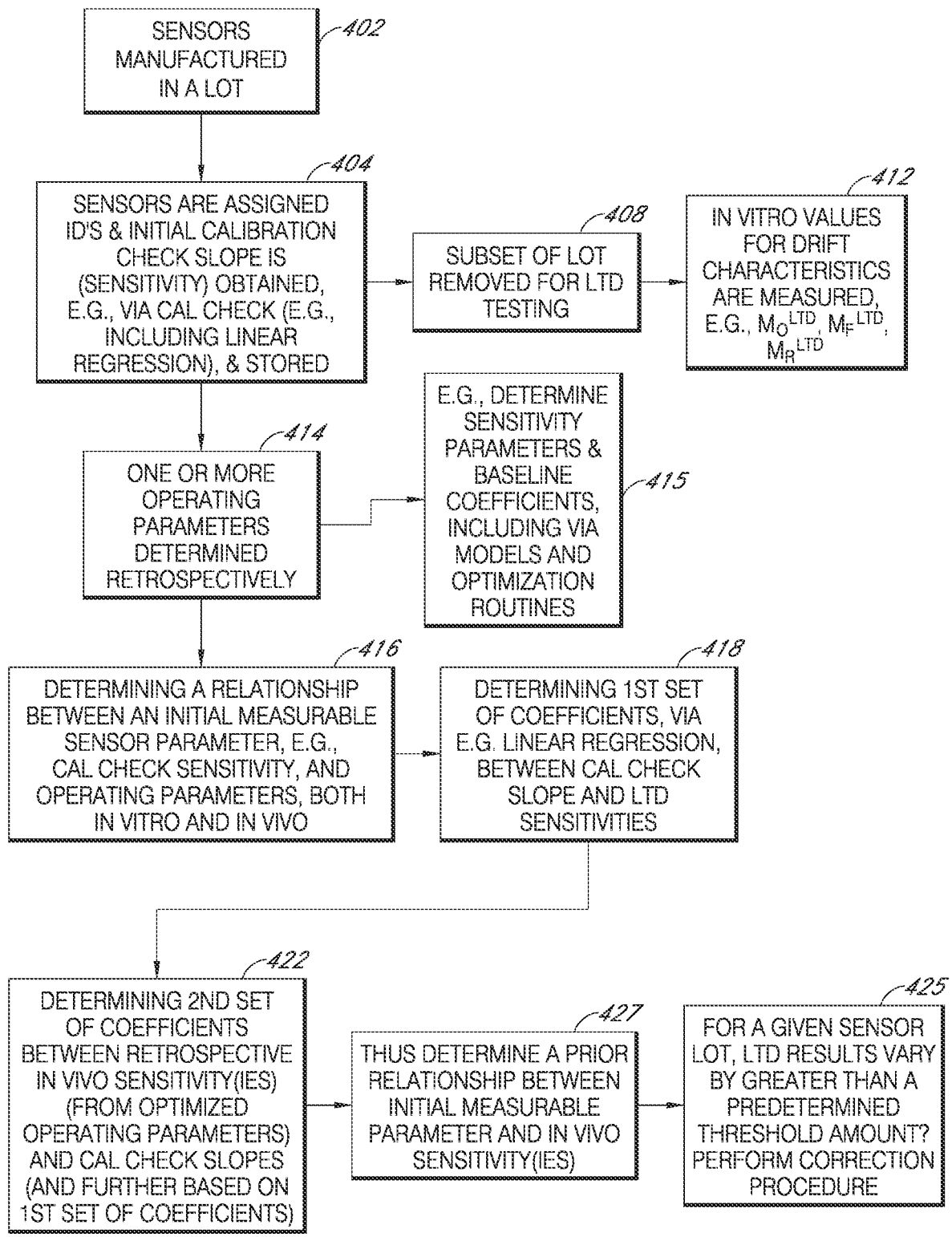
FIG. 4 illustrates an exemplary flowchart of a method according to present principles.

Thus, in a first step, and referring to FIG. 4, a lot of sensors is manufactured (step 402). In a second step, the sensors from the lot are assigned identification codes and a characteristic or initial measurable parameter of the sensors is measured and stored, e.g., an initial in vitro calibration check slope, via the cal check procedure described above (step 404). A subset of the lot of sensors is removed (step 408) from the lot, with the purpose being to test for operating parameters and in particular long term drift characteristics (step 412), e.g., in order to track and trend a variation in sensitivity drift profile. As this test is largely destructive, the sensors in this subset are generally not re-used in patients. In one exemplary implementation, the test is run for 15 days. For example, from a first bath (0 mg/dL analyte concentration, e.g. glucose), a lot median baseline is calculated and subtracted from the signal of each sensor in a second bath (e.g., 250 mg/dL glucose). For each raw count a sensitivity value is calculated. In this way, the test determines values for parameters $m_{0,LTD}$, $m_{F,LTD}$ and $m_{R,LTD}$ using routines described in the following sections.

To generate operating parameters $m_0$, $m_F$ and $m_R$ for each sensor, and in particular those related to in vivo values, as opposed to the in vitro values determined on the bench, equations and relationships are used as described below, the purpose of the steps being to determine, prospectively, the in vivo sensitivity values of a given sensor at a given moment t post insertion. While retrospective analysis of the operating parameters of sensors of the same type can be used to determine certain of the same for a given sensor, the sensitivity and baseline values for a given (subsequent) sensor should be based on a specifically measured parameter of the given sensor, and in this way parameters determined by population data and/or clinical trial data may be "specified" or adapted to the given sensor. The cal check sensitivity is one such specific initial measurable parameter, although others may also be employed. Where the cal check sensitivity is employed, systems and methods according to present principles determine the coefficients of the linear correlation between the cal check sensitivity and the in vivo operating parameters of the sensors. The linear coefficients are then used prospectively in subsequent sensors to predict the in vivo sensitivity profiles based on the cal check sensitivity of individual sensors.

As a precursor to deriving the aforementioned linear coefficients that relate cal check sensitivity to in vivo operating parameters, a next step is to determine one or more in vivo operating parameters empirically using a retrospective analysis (step 414), e.g., to determine sensitivity parameters and baseline coefficients, including via use of developed models and optimizations/fitting routines (step 415). This step includes sub-steps of determining appropriate sensitivity and baseline models, and optimizing a set of operating parameters for such models, appropriately initialized, based on a cost function.

The following additional terms are used and defined below for use in systems and methods according to present principles:

TABLE I

| | |
|---|---|
| CC | cal check slopes (pA/(mg/dL)), also denoted interchangeably as $m_{CC}$. |
| LTD | Long Term Drift test, e.g., generally at just one analyte concentration value, also termed a constant drift test |
| x(t) | Blood glucose (mg/dL), and the estimated glucose value (EGV) is $\hat{x}(t)$. |
| y(t) | CGM sensor current (pA). |
| m(t) | Sensor sensitivity (pA/(mg/dL)) at time t, and model-predicted sensitivity is $\hat{m}(t)$. |
| $m_0$ | Initial sensitivity (pA/(mg/dL)) at time t = 0. |
| $m_F$ | Final sensitivity (pA/(mg/dL)) at time t = ∞. |
| $m_R$ | Rate of exponential drift (1/day). |
| λ | Ratio between fast and slow components in the dual-exponential sensitivity model. |
| $B_1(t)$ | Non-glucose baseline (pA) of the sensor, and model-predicted baseline is $\hat{B}_1(t)$. |
| $B_2(t)$ | Compartmental bias (mg/dL) between glucose concentration in the local tissue surrounding the sensor and the blood glucose, and the model-predicted bias is $\hat{B}_2(t)$. |
| $b_1$ | Constant baseline (pA). |
| $b_2$ | Asymptotic magnitude (pA) of baseline rise due to membrane degradation. |
| $b_3$ | Onset/transition time (days) of baseline rise due to membrane degradation. |
| $b_4$ | Drift rate (1/day) of baseline rise due to membrane degradation. |
| $b_5$ | Initial magnitude (pA) of fast electrochemical break-in. |
| $b_6$ | Drift rate (1/day) of fast electrochemical break-in. |
| $b_7$ | Initial magnitude (pA) of slow electrochemical break-in. |
| $b_8$ | Drift rate (1/day) of slow electrochemical break-in. |
| $b_9$ | Initial magnitude (pA or mg/dL depending on model) of compartmental bias. |
| $b_{10}$ | Final magnitude (pA or mg/dL depending on model) of compartmental bias. |
| $b_{11}$ | Drift rate (1/day) of the disappearing compartmental bias. |

The coefficients above are termed operating parameters, and a first step of factory calibration is the determination of one or more of these operating parameters for a particular type or design of sensors, where the determination is based on retrospective data (step 414), e.g., from prior bench tests or clinical data. The coefficients above are generally developed with numerical analysis, as will be described, and have starting or initial values based on bench tests or clinical studies. In particular, the fundamental assumption about the physical process of a sensor generating signals according to analyte concentration is:

$y(t) = m(t) \cdot (x(t) + B_2(t)) + B_1(t)$, since the actual m(t), $B_1(t)$ and $B_2(t)$ are difficult to measure in vivo, we may rely on model predictions to perform calibration, therefore the EGV is given by reversing this equation and substituting in model-prediction terms accordingly:

$$\hat{x}(t) = \frac{y(t) - \hat{B}_1(t)}{\hat{m}(t)} - \hat{B}_2(t) \quad \text{Eqn. (1)}$$

The sensitivity profile model using a single exponential (see FIG. 5) is given below in (pA/(mg/dL)):

$$\hat{m}(t) = m_0 + (m_F - m_0) \cdot (1 - \exp\{-m_R \cdot t\}) \quad \text{Eqn. (2)}$$

Figure 6:
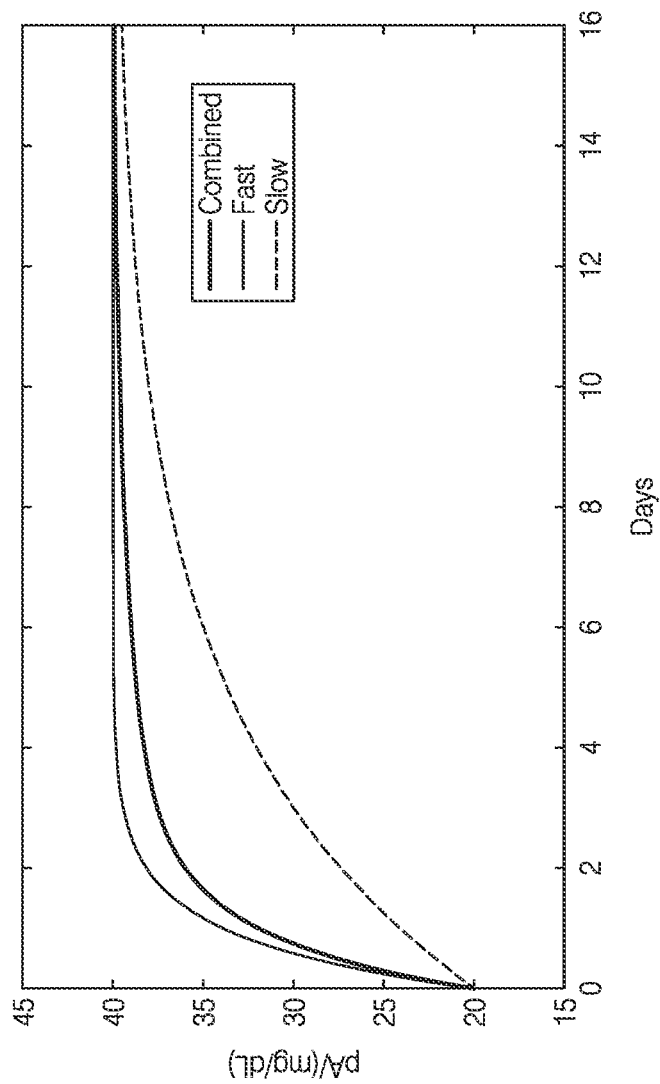
FIG. 6 illustrates an exemplary change of sensitivity over time, in particular showing a dual exponential model.

An alternative sensitivity model implemented in the joint-probability algorithm (JPA) described in the application incorporated by reference above is the convex combination of two exponential components, one fast and one slow (see FIG. 6):

$$\hat{m}(t) = m_0 + (m_F - m_0) \cdot [\lambda \cdot (1 - \exp\{-m_{R,1} \cdot t\}) + (1 - \lambda) \cdot (1 - \exp\{-m_{R,2} \cdot t\})] \quad \text{Eqn. (3)}$$

where in one implementation $\lambda = 0.8$ is the ratio between the two components, the fast drift rate is $$m_{R,1} = \frac{\ln(2)}{14/24},$$

and the slow drift rate is $$m_{R,2} = \frac{\ln(2)}{3}.$$

The above describes the model for sensitivity. In contrast, the baseline intercept model is divided into two components, the non-enzymatic break-in (in pA):

$$\hat{B}_1(t) = \quad \text{Eqn. (4)}$$
$$b_1 + \frac{b_2}{1 + \exp\left\{-\frac{t - b_3}{b_4}\right\}} + b_5 \cdot \exp\{-b_6 \cdot t\} + b_7 \cdot \exp\{-b_8 \cdot t\}$$

and the physiological negative bias is given by (in mg/dL):

$$\hat{B}_2(t) = b_9 + (b_{10} - b_9) \cdot (1 - \exp\{-b_{11} \cdot t\}) \quad \text{Eqn. (5)}$$

Figure 7:
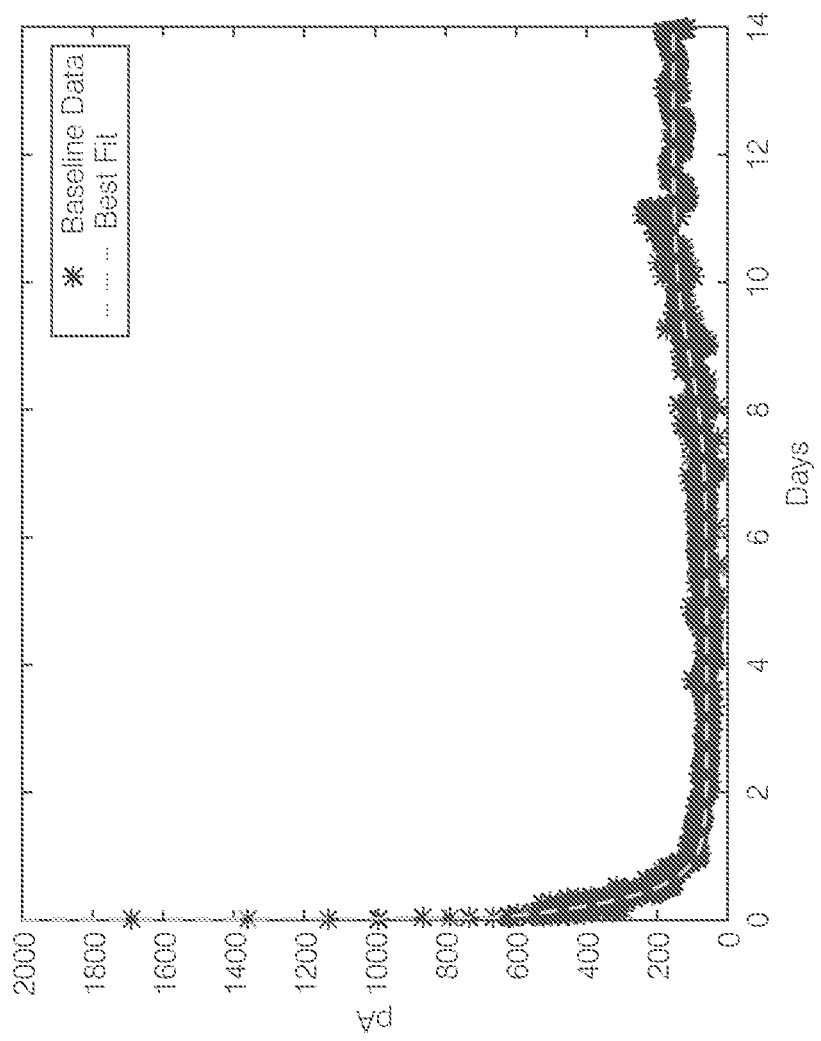
FIG. 7 illustrates the effect of non-enzyme break-in (measured without enzyme), and in particular shows data corresponding to the non-enzyme break-in model $B_1(t)$.
Figure 8:
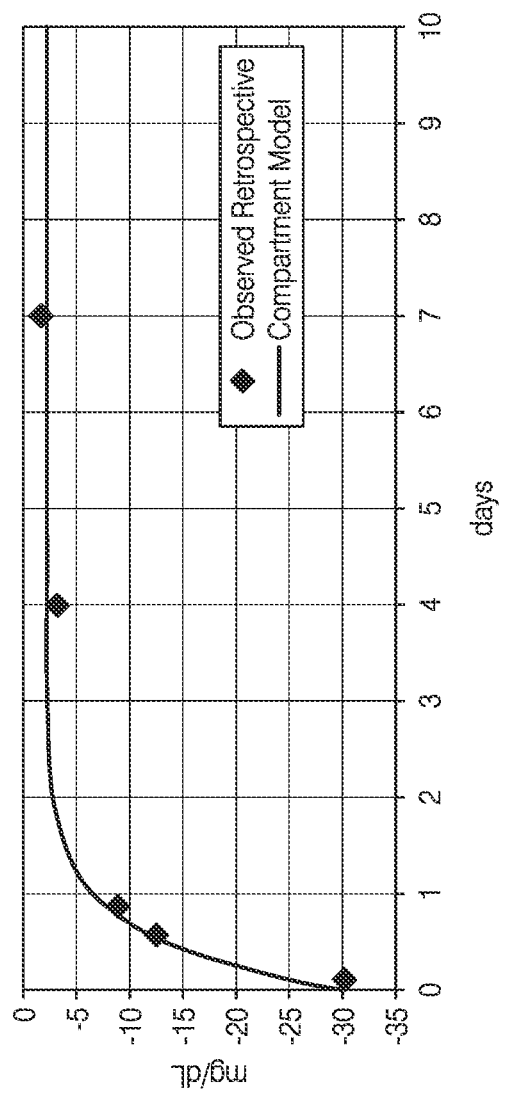
FIG. 8 illustrates an example of the physiological negative bias model $B_2(t)$.

An illustration of the model of the non-enzyme break-in baseline $B_1(t)$ is seen in one implementation in FIG. 7, and an illustration of the model of the physiological bias $B_2(t)$ is seen in FIG. 8. In exemplary studies, the models $\hat{B}_1(t)$ and $\hat{B}_2(t)$ have been seen to take the following parameters (described as vectors):

$B_1 = [b_1 b_2 b_3 b_4 b_5 b_6 b_7 b_8] = [61.1\ 95.0\ 8.8\ 0.7\ 10319.4\ 152.1\ 698.4\ 3.0]$ $B_2 = [b_9 b_{10} b_{11}] = [-30\ -2\ 1.8497]$

The relationships and models described above relating the slope or sensitivity values with each other and with the baseline may then be employed to determine values for a given sensor. In more detail, numerical analysis, and in particular retrospective model fitting methods, may then be employed to determine the optimum value of c for each given sensor, where c is a single vector with all the model parameters concatenated.

$c = [b_1 b_2 b_3 b_4 b_5 b_6 b_7 b_8 b_9 b_{10} b_{11} m_0 m_F m_R]^T$

An initial value with which to start the retrospective model fitting may be employed. For example, for one type of sensor, an initial value, e.g., from previous bench and clinical data, was found as:

$c_0 = [61.1\ 95.0\ 8.8\ 0.7\ 10319.4\ 152.1\ 698.4\ 3.0\ -30\ -2\ 1.8497\ 36.4\ 42.6\ 0.92]^T$

For another type of sensor, an initial value was found as:

$c_0' = [61.1\ 95.0\ 8.8\ 0.7\ 10319.4\ 152.1\ 698.4\ 3.0\ -30\ -2\ 1.8497\ 21.5\ 28.0\ 0.73]^T$

In this analysis, the first 11 digits of $c_0$ were estimated from non-enzyme sensor studies and other previous studies. The last three elements of $c_0$ were the lot average from a long-term drift test in a previous study. Values of these parameters may change with different sensors, or even as additional details are determined about the same sensors. These values may also be supplanted with values measured from the long term drift test for the particular subset of sensors from the particular lot. In this case baseline values may be determined from prior studies, and in this regard it is noted that baseline values tend to be more stable over time than sensitivity values. Where the dual exponential sensitivity model is employed, the last entry of c is the $\lambda$ parameter of that model.

Given the sensor raw current y(t) and c, the EGV can be calculated and coupled with an analyte reading from a gold-standard external reference (e.g. YSI, SMBG, HPLC, mass spectrometry and the like), which is termed a "matched pair", in order to evaluate accuracy of the EGV. The number of matched pairs may vary with session length and how compliant the host is, but in many cases 5-10 matched pairs per day may be used. A mean absolute relative difference (MARD) may be employed as a cost function and numerical analysis performed to search for the optimal parameter c* that minimizes MARD, initialized by $c_0$. For example, in one implementation, the Matlab® function "fminsearch" was used to search for the optimal parameter c*. The cost function may usually be referenced against the more readily available SMBG to account for a longer test period.

Where the MARD itself is minimized, the parameter fitting is unconstrained.

In another implementation, the parameter fitting can be constrained using prior knowledge about the sensors, in which case the minimization is of MARD and the deviation from expected $c_0$ to the actual parameter c. For example, for all the N matched-pairs of a sensor, a constrained cost function cost (c, c₀) can be defined based on the absolute relative difference (ARD):

$$\text{cost}(c, c_0) = \sum_{i=1}^{N} ARD_{t_i}(c) + |c - c_0|^2$$

$$ARD_{t_i}(c) = \left\| \left[ \frac{y(t_i) - \hat{B}_1(t_i, c)}{\hat{m}(t_i, c)} - \hat{B}_2(t_i, c) \right] \middle/ x(t_i) - 1 \right| \times 100\%$$

The rest of the fitting is the same as in the unconstrained scenario described above, e.g., using fminsearch method in Matlab®. The result of the fitting is the optimized c* vector.

It is noted however that while what has been described above is one possible definition of the cost function, there are actually many different ways to define the constrained cost function, which will strike a different balance between minimizing the error from EGV to true reference and minimizing the deviation from typical sensor behavior $c_0$ to the actual parameter c of a particular sensor.

In summary, the above description described one implementation of performing an optimization/cost function analysis to determine an optimized c vector for a given sensor using in vivo clinical data. A number of equations describing various relationships were employed to find the optimized c vector, which in turn determines an optimized $b_1$-$b_{11}$ and $m_0$, $m_R$, and $m_F$, for a particular given sensor. In this way, an optimized $B_1$ and $B_2$ may also be determined, from $b_1$-$b_8$ and $b_9$-$b_{11}$, respectively. From the in vitro long-term drift (destructive) test, $m_{0,LTD}$, $m_{R,LTD}$, and $m_{F,LTD}$ were also determined similarly.

For the in vitro long-term drift (LTD) test, the intercept model as well as the retrospective analysis is different from the in vivo counterpart. On the bench LTD, the intercept is measured using a different subset (or subsampling) of sensors from the same lot, tested in 0 mg/dL analyte solution. Because the in vitro intercept model is measured empirically, the initial parameter estimates for LTD only need to include the $m_{0,LTD}$, $m_{F,LTD}$, and $m_{R,LTD}$ (or λ) terms, and are simply:

$$c_0 = [21.5 \ 28.0 \ 0.73]^T$$

This initial (seed) parameter is used to initialize the search for the optimum parameter set, c*, that minimizes the following in vitro cost function for N raw data points per sensor:

$$\text{cost}_{TD}(c, c_0) = \sum_{i=1}^{N} ARD_{t_i}(c) + $$

$$|c(1, 2) - c_0(1, 2)|^2 + (0.5 \times \ln(c(3)))^{20} + (0.5 \times \ln(1 - c(3)))^{20}$$

where ARD is defined the same way as above.

In one implementation, a next step is to determine a relationship between an initial measurable parameter of the sensor and one or more of the in vivo and in vitro operating parameters of the sensor, such as between the cal check sensitivity of the sensor and an in vivo and/or in vitro sensitivity value (step 416). As will be described, this generally involves determining one or more sets of coefficients, and using the same to produce the in vivo sensitivity on a prospective and ongoing basis for subsequent sensors used in patients.

To start, in one implementation, an initial measurable value of the cal check slope is correlated with the determined LTD parameters (step 418). For example, in one implementation, the correlation is parameterized by the α, β, μ, and ν coefficients shown below in equations (I).

The cal check to LTD equations are:

$$\begin{cases} m_{0,LTD} = \alpha \cdot CC + \beta \\ m_{F,LTD} = \mu \cdot CC + \nu \end{cases} \quad (I.)$$

In order to derive this empirical correlation for subsequent use in prospective factory calibration, the sensor cal check and long-term drift data can be inserted into the set of equations (I) and data fitting analysis performed to determine α, β, μ, and ν. In one implementation, least squares linear regression is performed between the LTD sensitivity and the cal check sensitivity. In this regression, every matched pair may be a pair of (cal check, in vitro sensitivity) for one sensor, and for the lot of sensors, the linear regression may be performed to get, e.g., the α, β, μ, and ν.

The results of this regression are then used with the set of equations (II) to predict the in vivo operating parameters for each individual sensor.

That is, the cal check to in vivo sensitivity is parameterized with an additional set of coefficients γ, δ, ε, and σ in equations (II):

$$\begin{cases} m_{0,vivo} = \gamma \cdot \alpha \cdot CC + \delta \cdot \beta \\ m_{F,vivo} = \varepsilon \cdot \mu \cdot CC + \sigma \cdot \nu \end{cases} \quad (II.)$$

In each case, the above equations assume that there is a multiplicative scaling between the cal check-to-bench and the cal check-to-in vivo relationships.

In more detail, in order to establish the values of these coefficients in (II), retrospective analysis may be performed as described above based on the clinical and long-term drift data from previous studies, and from the determined c*, and analysis performed, e.g., ordinary least square (OLS) regression, to derive the linear relationship between the cal check slopes and $m_{0,VIVO}$ and $m_{F,VIVO}$ (step 422). In this regard it is noted that the c* determined using the techniques above, and in particular the $m_{0,VIVO}$, $m_{F,VIVO}$ and $m_{R,VIVO}$ (or λ) values determined (the last three operating parameters of c* vector), are from clinical studies as measured in vivo, and thus their use in the correlative equations (II) "tie in" the measured cal check values to the in vivo sensitivity values. For example, the in vivo $m_F$ is the second-to-last term or entry in c*. Thus the cal check sensitivity value, which can be measured for each sensor non-destructively, is correlated with the retrospective c* operating parameters through equations (II), and the same may then be used with a new measured cal check value to obtain the in vivo sensitivity values for a new (subsequent) sensor of the lot, where the assumption is made that the correlation found in equations (II) are representative of and holds for the entire lot.

In this way, once an initial value of an operating variable of the sensor, e.g., a cal check slope, is determined for a given sensor, the desired in vivo sensitivity values can be determined using at least the initial value of the operating variable and the determined relationship (step 427).

One or more of several schemes of factory calibration encoding may then be conducted.

Factory Calibration Encoding I

When a single exponential sensitivity model, e.g., equation (2), is used for parameter fitting, the drift rate may be fixed as, e.g., $m_R=0.9$. In this case, the values of the OLS linear coefficients may be determined to be:

$$\begin{cases} \alpha = 0.8883, \beta = 2.9320 \\ \mu = 0.9081, \nu = 8.7139 \end{cases}$$

$$\begin{cases} \gamma = 0.8882, \delta = 2.7064 \\ \varepsilon = 0.9907, \sigma = 1.2318 \end{cases}$$

$$\begin{cases} \gamma \cdot \alpha = 0.7890, \delta \cdot \beta = 7.9353 \\ \varepsilon \cdot \mu = 0.8997, \sigma \cdot \nu = 10.7339 \end{cases}$$

Figure 9B:
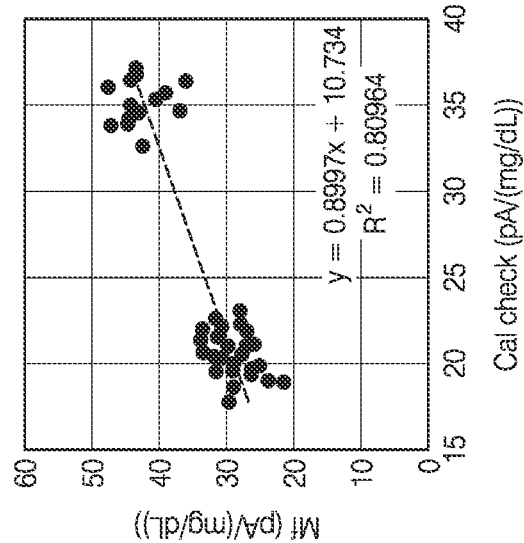
FIGS. 9A and 9B illustrate a retrospective fit using the single exponential sensitivity model.
Figure 9A:
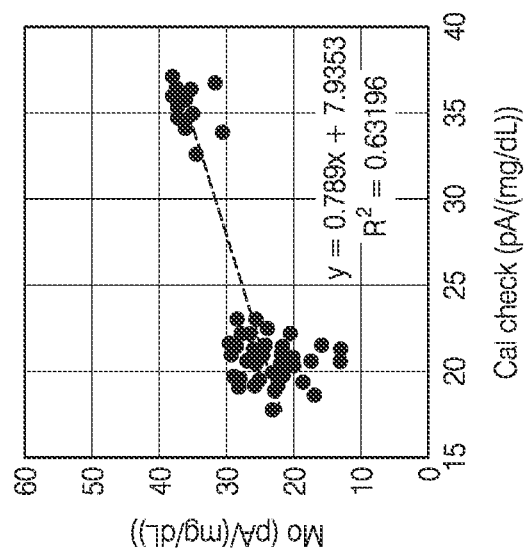

FIGS. 9A and 9B illustrate an exemplary retrospective OLS fit using the single exponential sensitivity model noted above.

Where the dual exponential sensitivity model (equation (3)) is used, the ratio between fast and slow components may be fixed as λ=0.8, and the values of the OLS linear coefficients may be determined to be:

$$\begin{cases} \alpha = 0.8883, \beta = 2.9320 \\ \mu = 0.9081, \nu = 8.7139 \end{cases}$$

$$\begin{cases} \gamma = 1.0460, \delta = 1.5754 \\ \varepsilon = 0.9866, \sigma = 1.3075 \end{cases}$$

$$\begin{cases} \gamma \cdot \alpha = 0.9292, \delta \cdot \beta = 4.6191 \\ \varepsilon \cdot \mu = 0.8959, \sigma \cdot \nu = 11.3930 \end{cases}$$

Figure 10B:
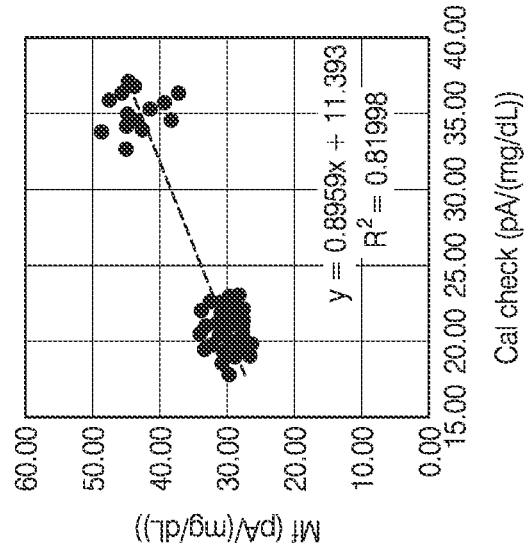
FIGS. 10A and 10B illustrate a retrospective fit using the dual exponential sensitivity model.
Figure 10A:
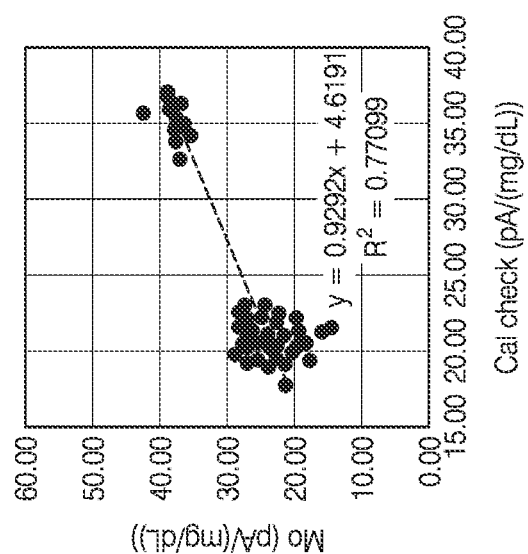

FIGS. 10A and 10B illustrate an exemplary retrospective OLS fit using the dual exponential sensitivity model noted above.

Figure 11A:
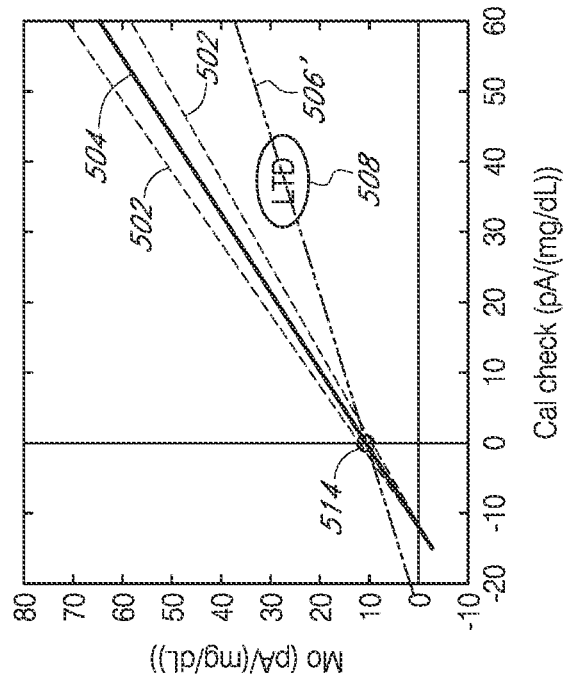
FIGS. 11A and 11B illustrate two strategies for handling scenarios deviating significantly from an expected linear relationship between a cal check procedure and in vivo sensitivity parameters.
Figure 11B:
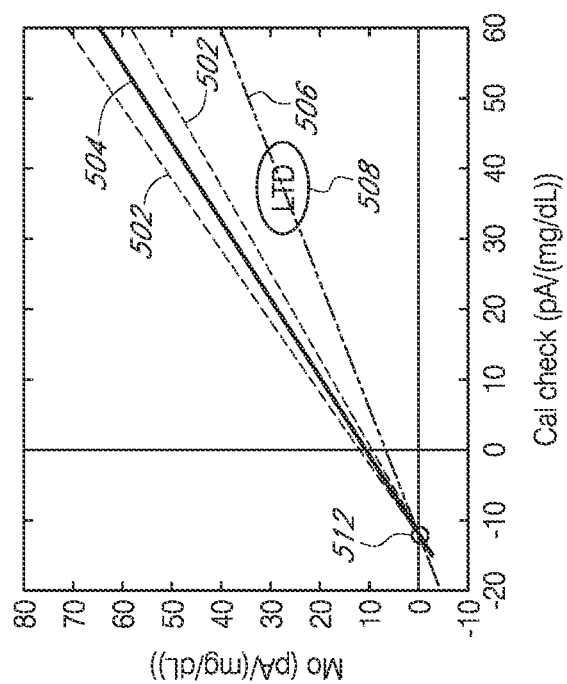

If long-term drift test results from new incoming sensor lots deviate substantially, e.g., by greater than 5%, 10%, 20%, or other measure, from the expected linear relationship (see, e.g., the ellipsoid in FIGS. 11A and 11B), then remedial strategies may be employed to estimate a new linear predictor of the in vivo sensitivity profile for factory calibration for a given sensor lot (step 425). Two remedial strategies are described below.

Referring to the figures, line 504 indicates an expected linear relationship estimated using the methods above. Lines 502 indicate ±10% bounds around the expected linear relationship. Ellipsoids 508 indicate long-term drift results that deviate more than a predetermined amount, e.g., greater than ±10%, away from the expected relationship. Circles indicate an intercept that is maintained in a new linear relationship for handling the exceptions. Lines 506 and 506 indicate the new linear regression.

In a first strategy, the x-axis intercept is maintained, and thus circle 512 is employed along with new linear relationship 506. In a second strategy, the y-axis intercept is maintained, and thus circle 514 is employed, along with the new linear relationship 506'.

Once a suitable relationship is determined between an initial measurable parameter, e.g., cal check sensitivity, and an in vivo sensitivity, the same relationship may be employed to prospectively determine in vivo sensitivity for subsequent sensors of the lot.

Figure 12:
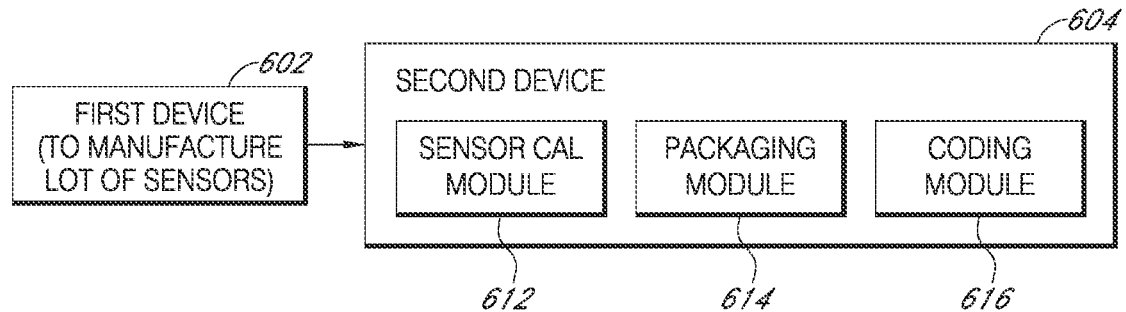
FIG. 12 illustrates a system to manufacture and calibrate a lot of sensors.

For example, and referring to FIG. 12, a first device 602 may be employed to manufacture a lot of sensors, and then a second device 604, subsequent on the assembly line, may be used to develop a calibration for the manufactured sensors. The second device 604 may include a sensor calibration module 612 which performs the steps above to measure the initial measurable parameter and to determine the in vitro sensitivity therefrom. A coding module 616 may be employed to develop a calibration indicator which can be associated with the manufactured sensor, where the calibration indicator can be used by a user to calibrate the sensor once it is received.

Figure 13:
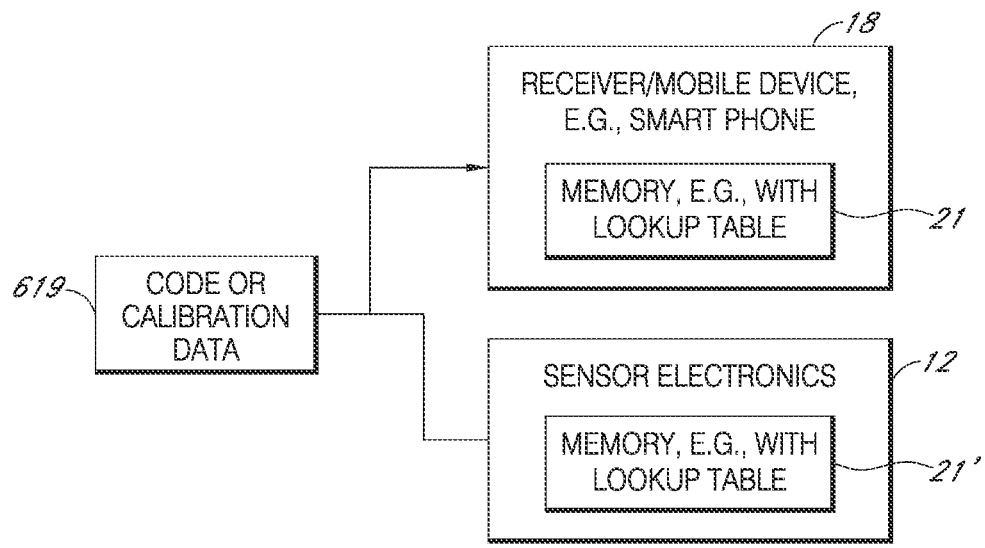
FIG. 13 schematically illustrates code transmission to sensor electronics or to a receiver/mobile device.

Referring in addition to FIG. 13, the calibration indicator may be in the form of a code 619 that is entered into either sensor electronics 12 or a mobile device/receiver 18 to provide the calibration information. A simple alphanumeric code, e.g., "A", "B", or the like, may be keyed to a value in a lookup table (21 or 21') stored in the mobile device or in the sensor electronics, respectively. In some cases, the code may contain the calibration information, such as sensitivity values. In these implementations, the code may be embodied by an RFID tag or NFC tag, which may be "swiped" by the sensor electronics or mobile device to transfer the code. In a similar way, the code may be embodied by a barcode or other optically, electrically, or mechanically readable medium. Other ways of transferring calibration information will be understood given this teaching.

Figure 14:
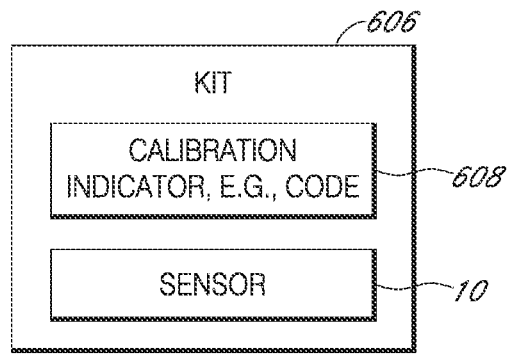
FIGS. 14 and 15 schematically illustrate kits in which systems and methods according to present principles may be packaged.
Figure 15:
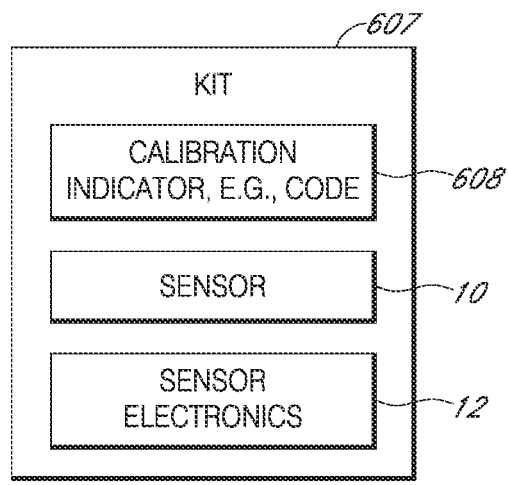

Referring back to FIG. 12, a packaging module 614 may form a part of the second device 604, the packaging module serving to package the sensor and calibration indicator either individually or along with a sensor electronics device. Referring to FIG. 14, a kit 606 may include a sensor 10 and a calibration indicator 608 as described above. In an alternative implementation, and referring to FIG. 15, a kit 607 may include a sensor 10, a calibration indicator 608 as described above, as well as a sensor electronics device 12. In many implementations, the sensor electronics device 12 forms a transmitter that is mechanically configured to be physically coupled to the sensor.

What has been described are systems and methods for achieving factory calibration for sensors, using an initial measured value of the sensor and a relationship between the initial measured value and one or more in vivo sensitivity parameters.

In one preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. patent application Ser. No. 11/543,396 filed Oct. 4, 2006, co-pending U.S. patent application Ser. No. 11/691,426 filed on Mar. 26, 2007, and co-pending U.S. patent application Ser. No. 11/675,063 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIG. 2) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, WiFi, Bluetooth®, RFID, NFC, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred, 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

The system and method may be fully implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file-storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi-connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where factory calibration schemes are contemplated, the plural inputs may allow plural users to input relevant data at the same time.

What is claimed is:

1. A system for calibrating an analyte concentration sensor, the sensor being a member of a manufactured lot of sensors, in which one or more operating parameters of the sensors of the lot have been determined, the determining of the operating parameters based on retrospective data, the operating parameters corresponding to at least a sensitivity of the sensors, the operating parameters representing in vivo values, the system comprising a device configured to perform operations comprising:
    measuring an in vitro sensitivity of a first sensor in the lot of sensors;
    measuring at least one drift characteristic for at least one sensor in the lot of sensors, the at least one drift characteristic being representative of the sensors in the lot of sensors;
    determining at least a first coefficient for relating the in vitro sensitivity of the first sensor with the at least one drift characteristic;
    determining an in vitro sensitivity of a second sensor in the lot of sensors; and
    determining, using at least the first coefficient and the in vitro sensitivity of the second sensor, a predicted in vivo sensitivity of the second sensor.

2. The system of claim 1, wherein the measuring at least one drift characteristic for the at least one sensor in the lot includes measuring at least two long-term drift characteristics for sensors of the lot, the long-term drift characteristics including an initial long-term drift-test sensitivity and a final long-term drift-test sensitivity.

3. The system of claim 2, the operations further comprising determining a long-term drift-test rate of change sensitivity based on the initial long-term drift-test sensitivity and the final long-term drift-test sensitivity.

4. The system of claim 2, wherein the device comprises a solution containing an analyte at a known concentration and wherein measuring of the initial long-term drift-test sensitivity and the final long-term drift-test sensitivity is performed by disposing the at least one sensor in the solution.

5. The system of claim 2, the operations further comprising storing the predicted in vivo sensitivity of the second sensor for subsequent transmission to sensor electronics associated with the second sensor, or transmitting the predicted in vivo sensitivity of the second sensor to sensor electronics associated with the second sensor.

6. The system of claim 1, wherein the at least one drift characteristic is characterized by a sensitivity model defined by a set of sensitivity parameters, wherein the sensitivity model includes an exponential function.

7. The system of claim 6, wherein the function is a single exponential function.

8. The system of claim 6, wherein the function is a dual exponential function.

9. The system of claim 6, wherein the set of sensitivity parameters includes m0 or mF or both.

10. The system of claim 9, wherein the sensitivity model further comprises mR.

11. The system of claim 1, wherein the determining the in vitro sensitivity of the second sensor in the lot of sensors comprises measuring a parameter of the second sensor.

12. The system of claim 11, wherein the parameter is a membrane thickness.

13. The system of claim 1, wherein the determining the in-vitro sensitivity of the second sensor further comprises:
    measuring an output signal of the second sensor at a plurality of values of an analyte concentration, and
    performing a linear regression procedure using the measured output signals and measured values of the analyte concentration.

* * * * *